(12) United States Patent
Jeschke et al.

(10) Patent No.: US 8,404,855 B2
(45) Date of Patent: Mar. 26, 2013

(54) SUBSTITUTED ENAMINOCARBONYL COMPOUNDS

(75) Inventors: Peter Jeschke, Bergisch Gladbach (DE); Robert Velten, Langenfeld (DE); Thomas Schenke, Bergisch Gladbach (DE); Otto Schallner, Monheim (DE); Michael Edmund Beck, Monheim (DE); Rolf Pontzen, Leichlingen (DE); Olga Malsam, Rösrath (DE); Udo Reckmann, Köln (DE); Ralf Nauen, Langenfeld (DE); Ulrich Görgens, Ratingen (DE); Leonardo Pitta, Leverkusen (DE); Thomas Müller, Offenbach (DE); Christian Arnold, Langenfeld (DE); Erich Sanwald, Kiel (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 13/334,949

(22) Filed: Dec. 22, 2011

(65) Prior Publication Data
US 2012/0157498 A1      Jun. 21, 2012

Related U.S. Application Data

(63) Continuation of application No. 12/295,355, filed as application No. PCT/EP2007/002386 on Mar. 19, 2007, now Pat. No. 8,106,211.

(30) Foreign Application Priority Data

Mar. 31, 2006   (DE) .......................... 10 2006 015 467

(51) Int. Cl.
| | |
|---|---|
| *A61K 31/38* | (2006.01) |
| *A61K 31/34* | (2006.01) |
| *C07D 409/00* | (2006.01) |
| *C07D 405/00* | (2006.01) |
| *C07D 213/61* | (2006.01) |

(52) U.S. Cl. .................. 546/279.7; 546/281.7; 546/345; 514/444; 514/473

(58) Field of Classification Search ........................ None
See application file for complete search history.

(56) References Cited

U.S. PATENT DOCUMENTS

| 5,935,981 | A  | * | 8/1999  | Minamida et al. ............ 514/365 |
| 6,303,638 | B1 | * | 10/2001 | Latli et al. ..................... 514/340 |
| 7,417,150 | B2 |   | 8/2008  | Jeschke et al. |
| 2008/0280953 | A1 |   | 11/2008 | Gorgens et al. |

FOREIGN PATENT DOCUMENTS

| EP | 0 539 588 | 5/1993 |
| WO | 02085870 | 10/2002 |
| WO | 2006/037475 | 4/2006 |

OTHER PUBLICATIONS

CAPLUS 1989:553338.*
Richard B. Silverman "The Organic Chemistry of Drug Design and Drug Action". Elsevier Academic Press (2004), pp. 34 and 86.
Timothy C. Johnson et al. "Penoxsulam-Structure-activity relationships of Triazolopyrimidine Sulfonamides", Bioorganic & Medical Chemistry 17 (2009), pp. 4230-4240.
Clemens Lamberth "Alkyne Chemistry in Crop Protection", Bioorganic & Medicinal Chemistry 17 (2009), pp. 4047-4063.
John W. Lyga et al. "Synthesis and Chemistry of Agrochemicals VII", American Chemical Society (2007), pp. 209-215.
I. Yamamoto et al. "Nicotinoid Insecticides and the Nicotinic Acetylcholine Receptor", Springer, (1997), pp. 148-155.
T. P. Selby et al., 228th ACS National Meeting, Philadelphia, PA, U.S.A., Aug. 22-26, (2004); Abstract of Papers AGRO-001.
Gilchrist, T. "Heterocyclic Chemistry," Addison Wesley Longman 1997, pp. 258-260.

* cited by examiner

*Primary Examiner* — David K O'Dell
*Assistant Examiner* — Heidi Reese
(74) *Attorney, Agent, or Firm* — Baker Donelson Bearman Caldwell & Berkowitz, PC

(57) ABSTRACT

The present invention relates to novel substituted enaminocarbonyl compounds, to processes for their preparation and to their use for controlling animal pests, especially arthropods, in particular insects.

6 Claims, No Drawings

SUBSTITUTED ENAMINOCARBONYL COMPOUNDS

CROSS REFERENCE TO RELATED APPLICATIONS

This application is a continuation application of U.S. application Ser. No. 12/295,355, filed Mar. 11, 2009, now U.S. Pat. No. 8,106,211, which claims priority to §371 National Stage Application of PCT/EP2007/002386 filed Mar. 19, 2007 which claims priority from German Application 10 2006 015 467.3 filed Mar. 31, 2006, the content of each this application is hereby incorporated by reference in their entirety.

BACKGROUND OF THE INVENTION

1. Field of the Invention

The present application relates to novel substituted enaminocarbonyl compounds, to processes for their preparation and to their use for controlling animal pests, especially arthropods, in particular insects.

2. Description of Related Art

Substituted enaminocarbonyl compounds are already known as insecticidally active compounds (cf. EP 0539588 A1).

SUMMARY OF THE INVENTION

This invention now provides novel compounds of the formula (I)

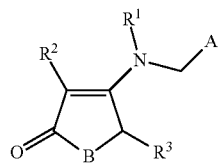

(I)

in which
A represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is optionally substituted in the 2-position by chlorine or methyl,
B represents oxygen, sulphur or methylene,
$R^1$ represents haloalkyl, haloalkenyl, halocycloalkyl or halocycloalkylalkyl,
$R^2$ represents hydrogen or halogen and
$R^3$ represents hydrogen or alkyl.

DETAILED DESCRIPTION OF A PREFERRED EMBODIMENT

Furthermore, it has been found that the novel substituted compounds of the formula (I) are obtained when
a) compounds of the formula (II)

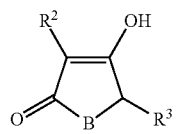

(II)

in which
B, $R^2$ and $R^3$ are as defined above
are reacted with compounds of the formula (III)

$$HN(R^1)-CH_2-A \qquad (III)$$

in which
A and $R^1$ are as defined above,
if appropriate in the presence of a suitable diluent and if appropriate in the presence of an acidic auxiliary (process 1), or when
b) compounds of the formula (Ia)

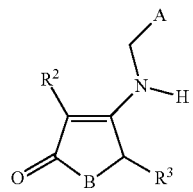

(Ia)

in which
A, B, $R^2$ and $R^3$ are as defined above
are reacted with compounds of the formula (IV)

$$E-R^1 \qquad (IV)$$

in which
$R^1$ is as defined above and
E represents a suitable leaving group such as, for example, halogen (in particular bromine, chlorine, iodine) or O-sulphonylalkyl and O-sulphonylaryl (in particular O-mesyl, O-tosyl),
if appropriate in the presence of a suitable diluent and if appropriate in the presence of an acid acceptor (process 2), or when
c) compounds of the formula (II)

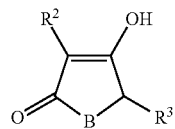

(II)

in which
B, $R^2$ and $R^3$ are as defined above,
are, in a first reaction step, reacted with compounds of the formula (V)

$$H_2N-R^1 \qquad (V)$$

in which
$R^1$ is as defined above
if appropriate in the presence of a suitable diluent and if appropriate in the presence of an acidic auxiliary, and the resulting compounds of the formula (VI)

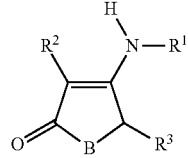

(VI)

in which
B, $R^1$, $R^2$ and $R^3$ are as defined above
are then, in a second reaction step, reacted with compounds of the formula (VII)

$$E-CH_2-A \qquad (VII)$$

in which

E and A are as defined above, if appropriate in the presence of a suitable diluent and if appropriate in the presence of an acid acceptor (process 3).

Finally, it has been found that the novel compounds of the formula (I) have pronounced biological properties and are suitable especially for controlling animal pests, in particular insects, arachnids and nematodes encountered in agriculture, in forests, in the protection of stored products and in the protection of materials, and also in the hygiene sector.

Depending inter alia on the nature of the substituents, the compounds of the formula (I) may be present as geometrical and/or as optically active isomers or corresponding isomer mixtures of varying composition. The invention relates both to the pure isomers and the isomer mixtures.

The formula (I) provides a general definition of the compounds according to the invention.

Preferred substituents or ranges of the radicals given in the formulae mentioned above and below are illustrated below.

A preferably represents 6-fluoropyrid-3-yl, 6-chloropyrid-3-yl, 6-bromopyrid-3-yl, 6-methyl-pyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl.

B preferably represents oxygen or methylene.

$R^1$ preferably represents fluorine-substituted $C_1$-$C_5$-alkyl, $C_2$-$C_5$-alkenyl, $C_3$-$C_5$-cycloalkyl or $C_3$-$C_5$-cycloalkylalkyl.

$R^2$ preferably represents hydrogen or halogen (where halogen represents in particular fluorine or chlorine), $R^3$ preferably represents hydrogen or methyl.

A particularly preferably represents the radical 6-fluoropyrid-3-yl, 6-chloropyrid-3-yl, 6-bromopyrid-3-yl, 6-chloro-1,4-pyridazin-3-yl, 2-chloro-1,3-thiazol-5-yl, B particularly preferably represents oxygen or methylene.

$R^1$ particularly preferably represents 2-fluoroethyl, 2,2-difluoroethyl, 2-fluorocyclopropyl.

$R^2$ particularly preferably represents hydrogen.

$R^3$ particularly preferably represents hydrogen.

A very particularly preferably represents the radical 6-chloropyrid-3-yl, 6-bromopyrid-3-yl or 6-chloro-1,4-pyridazin-3-yl, B very particularly preferably represents oxygen.

$R^1$ very particularly preferably represents 2,2-difluoroethyl.

$R^2$ very particularly preferably represents hydrogen.

$R^3$ very particularly preferably represents hydrogen.

In a special group of compounds of the formula (I), A represents 6-chloropyrid-3-yl

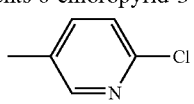

In a further special group of compounds of the formula (I), A represents 6-bromopyrid-3-yl

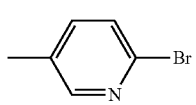

In a further special group of compounds of the formula (I), A represents 6-chloro-1,4-pyridazin-3-yl

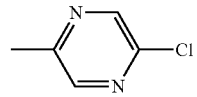

In a further special group of compounds of the formula (I), A represents 2-chloro-1,3-thiazol-5-yl

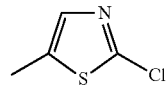

Hereinbelow, a further group of preferred radicals is defined in which

A represents pyrid-3-yl which is substituted in the 6-position by fluorine, chlorine, bromine, methyl or trifluoromethyl or represents 2-chloropyrazin-5-yl or represents 2-chloro-1,3-thiazol-5-yl, B represents oxygen, sulphur or methylene, $R^1$ represents halo-$C_1$-$C_3$-alkyl, halo-$C_2$-$C_3$-alkenyl, halocyclopropyl (where halogen represents in particular fluorine or chlorine), $R^2$ represents hydrogen or halogen and $R^3$ represents hydrogen or methyl.

A preferably represents 6-fluoropyrid-3-yl, 6-chloropyrid-3-yl, 6-bromopyrid-3-yl, 6-trifluoromethylpyrid-3-yl, 2-chloropyrazin-5-yl or 2-chloro-1,3-thiazol-5-yl.

B preferably represents oxygen or methylene.

$R^1$ preferably represents difluoromethyl, 2-fluoroethyl, 2,2-difluoroethyl, 2-chloro-2-fluoroethyl, 3-fluoro-n-propyl, 2-fluorovinyl, 3,3-difluoroprop-2-enyl or 3,3-dichloroprop-2-enyl.

$R^2$ preferably represents hydrogen or halogen (where halogen represents in particular fluorine or chlorine).

$R^3$ preferably represents hydrogen.

A particularly preferably represents the radical 6-chloropyrid-3-yl or 6-bromopyrid-3-yl.

B particularly preferably represents oxygen.

$R^1$ particularly preferably represents 2-fluoroethyl or 2,2-difluoroethyl.

$R^2$ particularly preferably represents hydrogen.

$R^3$ particularly preferably represents hydrogen.

A very particularly preferably represents the radical 6-chloropyrid-3-yl or 6-bromopyrid-3-yl.

B very particularly preferably represents oxygen.

$R^1$ very particularly preferably represents 2,2-difluoroethyl.

$R^2$ very particularly preferably represents hydrogen.

$R^3$ very particularly preferably represents hydrogen.

In a special group of compounds of the formula (I), $R^3$ represents hydrogen, B represents oxygen and A represents 6-chloropyrid-3-yl

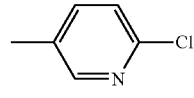

In a further special group of compounds of the formula (I), $R^3$ represents hydrogen, B represents oxygen and A represents 6-bromo-pyrid-3-yl

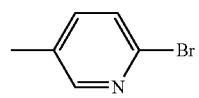

In a further special group of compounds of the formula (I), R³ represents hydrogen, B represents oxygen and A represents 6-fluoropyrid-3-yl

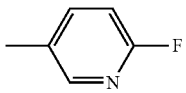

In a further special group of compounds of the formula (I), R³ represents hydrogen, B represents oxygen and A represents 6-trifluoromethyl-pyrid-3-yl

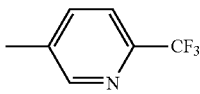

In a further special group of compounds of the formula (I), R³ represents hydrogen, B represents oxygen and A represents 2-chloro-1,3-thiazol-5-yl

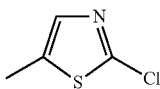

In a further special group of compounds of the formula (I), R² and R³ represent hydrogen, B represents oxygen and A represents 6-chloropyrid-3-yl

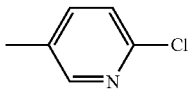

In a further special group of compounds of the formula (I), R² and R³ represent hydrogen, B represents oxygen and A represents 6-bromopyrid-3-yl

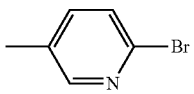

In a further special group of compounds of the formula (I), R² and R³ represent hydrogen, B represents oxygen and A represents 6-fluoropyrid-3-yl

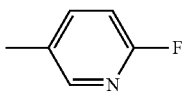

In a further special group of compounds of the formula (I), R² and R³ represent hydrogen, B represents oxygen and A represents 6-trifluoromethyl-pyrid-3-yl

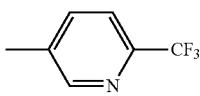

In a further special group of compounds of the formula (I), R² and R³ represent hydrogen, B represents oxygen and A represents 2-chloro-1,3-thiazol-5-yl

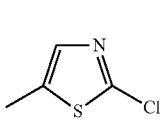

In a further special group of compounds of the formula (I), R² and R³ represent hydrogen, B represents methylene and A represents 6-chloropyrid-3-yl

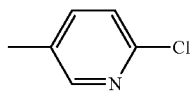

In a further special group of compounds of the formula (I), R² and R³ represent hydrogen, B represents methylene and A represents 6-bromopyrid-3-yl

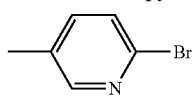

In a further special group of compounds of the formula (I), R² and R³ represent hydrogen, B represents methylene and A represents 6-fluoropyrid-3-yl

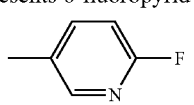

In a further special group of compounds of the formula (I), R² and R³ represent hydrogen, B represents methylene and A represents 6-trifluoromethyl-pyrid-3-yl

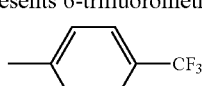

In a further special group of compounds of the formula (I), R² and R³ represent hydrogen, B represents methylene and A represents 2-chloro-1,3-thiazol-5-yl

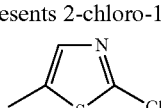

In a further special group of compounds of the formula (I), R¹ represents difluoromethyl, R² and R³ represent hydrogen and B represents oxygen.

In a further special group of compounds of the formula (I), R¹ represents 2-fluoroethyl, R² and R³ represent hydrogen and B represents oxygen.

In a further special group of compounds of the formula (I), R¹ represents 2,2-difluoroethyl, R² and R³ represent hydrogen and B represents oxygen.

In a further special group of compounds of the formula (I), R¹ represents difluoromethyl, R² and R³ represent hydrogen and B represents methylene.

In a further special group of compounds of the formula (I), R¹ represents 2-fluoroethyl, R² and R³ represent hydrogen and B represents methylene.

In a further special group of compounds of the formula (I), R¹ represents 2,2-difluoroethyl, R² and R³ represent hydrogen and B represents methylene.

The general or preferred radical definitions or explanations given above apply both to the end products and, correspondingly, to precursors and intermediates. These radical definitions can be combined with one another as desired, i.e. including combinations between the respective preferred ranges.

Preference according to the invention is given to compounds of the formula (I) which contain a combination of the meanings listed above as being preferred.

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

If, in the process 1 according to the invention for preparing the novel compounds of the formula (I), the compound of the formula (II) is, for example, tetronic acid and the compound of the formula (III) is N[6-chloropyridin-3-yl)methyl]-2,2-difluoroethane-1-amine, preparation process 1 can be represented by the reaction scheme I below:

Scheme I

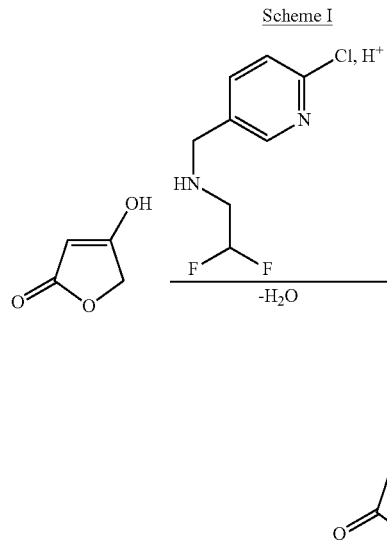

The formula (II) provides a general definition of the compounds required as starting materials for carrying out the process 1 according to the invention.

In this formula (II), B, $R^2$ and $R^3$ preferably represent those radicals which have already been mentioned in connection with the description of the compounds of the formula (I) according to the invention as preferred substituents.

Some of the compounds of the formula (II) can be obtained commercially or by methods known from the literature (cf., for example, compounds of the general formula (II) in which B represents oxygen: tetronic acids (Said, A. Speciality Chemicals Magazine (1984), 4(4), 7-8; Rao, Y. S. Chem. Rev. (1976), 76, 625-694; Tejedor, D.; Garcia-Tellado, F. Org. Preparations and Procedures International (2004), 36, 35-59; Reviews); compounds of the general formula (II) in which B represents sulphur: thiotetronic acids (Thomas, E. J. Special Publication—Royal Society of Chemistry (1988), 65 (Top. Med. Chem.), 284-307, Review), compounds of the general formula (II) in which B represents methylene: cyclopentane-1,3-dione (Schick, Hans; Eichhorn, Inge. Synthesis (1989), (7), 477-492, Review).

The formula (III) provides a general definition of the compounds furthermore to be used as starting materials for carrying out the process 1 according to the invention.

In formula (III), A and $R^1$ have the meanings already mentioned in connection with the description of the compounds of the formula (I) according to the invention.

Some of the compounds of the formula (III) can be obtained commercially or by methods known from the literature (cf., for example, S. Patai "The Chemistry of Amino Group", Interscience Publishers, New York, 1968; compounds of the general formula (III) in which $R^1$ represents hydrogen: primary amines, compounds of the general formula (III) in which IV represents haloalkyl, haloalkenyl or halocycloalkyl: secondary amines).

The compounds of the formula (III) can be prepared from compounds of the formula (VII) (cf. Scheme III further below).

Some of the compounds of the formula (VII) are commercially available, some are known, and they can be obtained by known methods (for example 2-chloro-5-chloromethyl-1,3-thiazole: DE 3 631 538 (1988), EP 446 913 (1991), EP 780 384 (1997), EP 775 700 (1997), EP 794 180 (1997), WO 9 710 226 (1997); 6-chloro-3-chloromethylpyridine: DE 3 630 046 A1 (1988), EP 373 464 A2 (1990), EP 373 464 A2 (1990), EP 393 453 A2 (1990), EP 569 947 A1 (1993); 6-chloro-3-bromomethylpyridine: I. Cabanal-Duvillard et al., Heterocycl. Commun. 5, 257-262 (1999); 6-bromo-3-chloromethylpyridine, 6-bromo-3-hydroxymethylpyridine: U.S. Pat. No. 5,420,270 A (1995); 6-fluoro-3-chloromethylpyridine: J. A. Pesti et al., J. Org. Chem. 65, 7718-7722 (2000); 6-methyl-3-chloromethylpyridine: EP 302389 A2, E. v der Eycken et al., J. Chem. Soc., Perkin Trans 25, 928-937 (2002); 6-trifluoromethyl-3-chloromethylpyridine: WO 2004/082616 A2; 2-chloro-5-chloromethylpyrazine: JP 05239034 A2).

General routes for preparing compounds of the formula (VII) are shown in reaction scheme II.

Scheme II

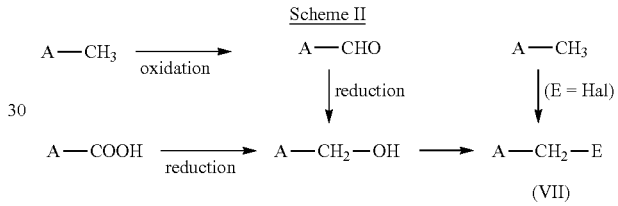

E = Hal, for example chlorine, bromine, iodine; O-tosyl, O-mesyl,
A = as defined above The heterocyclic carboxylic acids (A-COOH) can, for example, be converted by methods known from the literature into the corresponding heterocyclic hydroxymethyl compounds (A-CHSOH) which are then reacted by methods known from the literature to give activated heterocyclic hydroxymethyl compounds (A-CHS-E, E=OTosyl, OMesyl) or heterocyclic halomethyl compounds (A-CH$_2$-E, E=Hal). The latter can also be obtained from the corresponding methyl groupcontaining heterocycles (A-CH$_3$) using suitable halogenating agents known from the literature.

For preparing compounds of the formula (III), it is advantageous to react, for example, compounds of the formula (VII) in which A and E are as defined above with compounds of the formula (V) in which $R^1$ is as defined above, if appropriate in the presence of diluents and if appropriate in the presence of the basic reaction auxiliaries mentioned in preparation process 2 (cf. N-alkylation, Scheme III).

Scheme III

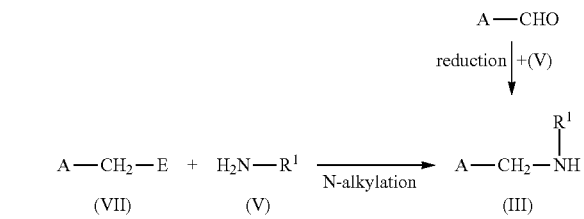

E = Hal, for example chlorine, bromine, iodine; O-tosyl, O-mesyl,
A = as defined above Some of the compounds of the formula (V) can be obtained commercially (cf., for example, 2-fluoroethylamine or 2,2- difluoroethylamine) or by methods known from the literature (cf., for example, 3-fluoro-n-propylamine: U.S. Pat. No. 6,252,087 B1; 3,3-difluoroprop-2-enylamine hydrochloride: WO 2001/007414 A1; 3,3-dichloroprop-2-enylamine: DE 2747814).

However, alternatively and in certain cases, it is also possible to prepare compounds of the formula (III) from the corresponding aldehydes (A-CHO) and compounds of the formula (V) by reductive amination (cf. Houben-Weyl, Methoden der Organischen Chemie, Vol. XI/1, Georg Thieme Verlag Stuttgart, p. 602). Some of the aldehydes (A-CHO) are commercially available (cf., for example, 6-chloronicotinaldehyde, 6-fluoronicotinaldehyde, 6-bromonicotinaldehyde, 2-chloro-1,3-thiazole-5-carbaldehyde), or they can be obtained by methods known from the literature (cf., for example, 6-methylnicotinaldehyde: EP 104876 A2; 2-chloropyrazine-5-carboxaldehyde: DE 3314196 A1).

In general, it is advantageous to carry out the preparation process 1 according to the invention in the presence of diluents. Diluents are advantageously employed in such an amount that the reaction mixture remains readily stirrable during the entire process. Suitable diluents for carrying out the process 1 according to the invention are all organic solvents which are inert under the reaction conditions.

Examples which may be mentioned are: halogenated hydrocarbons, in particular chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, n-butyl ether, anisole, phenetole, cyclohexyl methyl ether, dimethyl ether, diethyl ether, dipropylether, diisopropyl ether, di-n-butyl ether, diisobutyl ether, diisoamyl ether, ethylene glycol dimethyl ether, tetrahydrofuran, dioxane, dichlorodiethyl ether and polyethers of ethylene oxide and/or propylene oxide; amines, such as trimethylamine, triethylamine, tripropylamine, tributylamine, N-methylmorpholine, pyridine and tetramethylenediamine; nitrated hydrocarbons, such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile and also compounds, such as tetrahydrothiophene dioxide and dimethyl sulphoxide, tetramethylene sulphoxide, dipropyl sulphoxide, benzylmethyl sulphoxide, diisobutyl sulphoxide, dibutyl sulphoxide, diisoamyl sulphoxide; sulphones, such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons, such as pentane, hexane, heptane, octane, nonane and industrial hydrocarbons, for example white spirits with components having boiling points in the range of, for example, from 40° C. to 250° C., cymene, petroleum fractions having a boiling point interval of from 70° C. to 190° C., cyclohexane, methylcyclohexane, petroleum ether, ligroin, octane, benzene, toluene, chlorobenzene, bromobenzene, nitrobenzene, xylene; esters, such as methyl acetate, ethyl acetate, butyl acetate, isobutyl acetate, and also dimethyl carbonate, dibutyl carbonate, ethylene carbonate; amides, such as hexamethylenephosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine; ketones, such as acetone, acetophenone, methyl ethyl ketone, methyl butyl ketone.

It is also possible to use mixtures of the solvents and diluents mentioned for the process according to the invention.

However, preferred diluents for carrying out the process according to the invention are aromatic hydrocarbons, such as benzene, toluene, chlorobenzene, bromobenzene, nitrobenzene or xylene, in particular benzene and toluene.

The preparation of compounds of the formula (I) according to preparation process 1 is carried out by reacting compounds of the formula (II) in the presence of compounds of the formula (III), if appropriate in the presence of an acidic auxiliary and if appropriate in one of the diluents mentioned.

The reaction time is generally from 10 minutes to 48 hours. The reaction is carried out at temperatures between −10° C. and +200° C., preferably between +10° C. and 180° C., particularly preferably between 60° C. and 140° C. The reaction is preferably carried out under reaction conditions which allow water to be separated off or to be removed, for example with the aid of a water separator.

In principle, the reaction can be carried out under atmospheric pressure. The reaction is preferably carried out under atmospheric pressure or under pressures of up to 15 bar and, if appropriate, under an atmosphere of protective gas (nitrogen, helium or argon).

For carrying out the process 1 according to the invention, in general from 0.5 to 4.0 mol, preferably from 0.7 to 3.0 mol, particularly preferably from 1.0 to 2.0 mol of amino compound of the general formula (III) are employed per mole of the compound of the general formula (II).

Furthermore, for carrying out the process 1 according to the invention, in general catalytic amounts of an acidic auxiliary can be added.

Suitable acidic auxiliaries are, for example, p-toluenesulphonic acid or acetic acid.

After the reaction has gone to completion, the entire reaction mixture is concentrated. The products obtained after work-up can be purified in a customary manner by recrystallization, distillation under reduced pressure or column chromatography (cf. also the Preparation Examples).

If, in the process 2 according to the invention for preparing the novel compounds of the formula (I), the compound of the formula (Ia) is, for example, 4-[[(6-chloropyridin-3-yl)methyl]-amino]furan-2(5H)-one and the compound of the formula (IV) is 3-bromo-1,1-dichloroprop-1-ene, the preparation process 2 can be represented by reaction scheme IV below:

Scheme IV

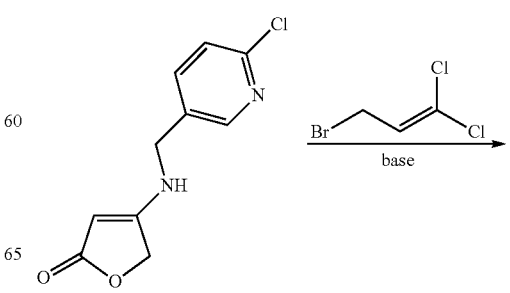

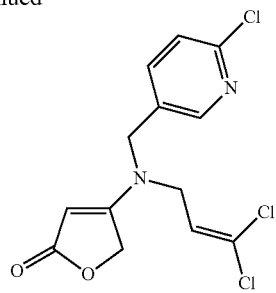

The formula (Ia) provides a general definition of the compounds required as starting materials for carrying out the process 2 according to the invention.

In this formula (Ia), A, B, R² and R³ preferably represent those radicals which have already been mentioned in connection with the description of the compounds of the formula (I) according to the invention as preferred substituents.

The compounds of the formula (Ia) can be obtained by preparation process 1, described further above, for example by reacting compounds of the formula (II) with compounds of the formula (III) in which R¹ represents hydrogen.

The formula (IV) provides a general definition of the compounds to be used in particular as starting materials for carrying out process 2 according to the invention.

In formula (IV), E and R¹ have the meanings already mentioned for substituents in connection with the description of the compounds of the general formula (I) according to the invention.

Some of the compounds of the formula (IV) are commercially available (cf., for example, chlorodifluoromethane, 1-bromo-2-fluoroethane, 2-bromo-1,1-difluoroethane, 2-bromo-1-chloro-1-fluoroethane, 1-bromo-3-fluoropropane, 3-bromo-1,1-difluoroprop-1-ene), or they can be obtained by methods known from the literature (cf., for example, 3-bromo-1,1-dichloroprop-1-ene: WO 8800183 A1 (1988); compounds of the general formula IV in which E represents halogen, such as chlorine, bromine and iodine: Houben-Weyl, Methoden der Organischen Chemie, Vol. V/3, Georg Thieme Verlag Stuttgart, p. 503 and Vol. V/4 p. 13, 517; compounds of the formula (IV) in which E represents mesylate: Crossland, R. K., Servis, K. L. J. Org. Chem. (1970), 35, 3195; compounds of the formula (IV) in which E represents tosylate: Roos, A. T. et al., Org. Synth., Coll. Vol. I, (1941), 145; Marvel, C. S., Sekera, V. C. Org. Synth., Coll. Vol. III, (1955), 366).

In general, it is advantageous to carry out the preparation process 2 according to the invention in the presence of diluents and in the presence of basic reaction auxiliaries.

Diluents are advantageously employed in such an amount that the reaction mixture remains readily stirrable during the entire process. Suitable diluents for carrying out the process 2 according to the invention are all inert organic solvents.

Preferred diluents for carrying out the process 2 according to the invention are ethers, such as methyl tert-butyl ether, n-butyl ether, anisole, phenetole, cyclohexyl methyl ether, diisopropyl ether, diisobutyl ether, diisoamyl ether, ethylene glycol dimethyl ether, tetrahydrofuran, dioxane, dichlorodiethyl ether and polyethers of ethylene oxide and/or propylene oxid, amides, such as hexamethylenephosphoric triamide, formamide, N-methylformamide, N,N-dimethylformamide, N,N-dipropylformamide, N,N-dibutylformamide, benzene, toluene, chlorobenzene, bromobenzene, nitrobenzene, xylene; ketones, such as acetone, acetophenone, methyl ethyl ketone or methyl butyl ketone.

Of course, it is also possible to use mixtures of the solvents and diluents mentioned for the process according to the invention.

However, preferred diluents for carrying out the process according to the invention are ethers, such as methyl tert-butyl ether or cyclic ethers, such as tetrahydrofuran and dioxane, amides, such as N,N-dimethylformamide, aromatic hydrocarbons, such as benzene or toluene; ketones, such as acetone, methyl ethyl ketone or methyl butyl ketone.

Suitable for use as basic reaction auxiliaries for carrying out the process 2 according to the invention are all suitable acid binders, such as amines, in particular tertiary amines, and also alkali metal and alkaline earth metal compounds.

Examples which may be mentioned are the hydroxides, hydrides, oxides and carbonates of lithium, sodium, potassium, magnesium, calcium and barium, furthermore other basic compounds, such as amidine bases or guanidine bases, such as 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methyl imidazole, N-methylpyrazole, N-methylmorpholine, N-methylhexamethylenediamine, pyridine, 4-pyrrolidinopyridine, 4-dimethylaminopyridine, chinoline, α-picoline, β-picoline, isochinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethyl-cyclohexylamine, 2,6-lutidine, 2,4-lutidine or triethyldiamine.

Preference is given to using hydrides of lithium or sodium.

The reaction time is generally from 10 minutes to 48 hours. The reaction is carried out at temperatures between −10° C. and +200° C., preferably between +10° C. and 180° C., particularly preferably between 60° C. and 140° C. In principle, the reaction can be carried out under atmospheric pressure. The reaction is preferably carried out under atmospheric pressure or under pressures of up to 15 bar and, if appropriate, under an atmosphere of protective gas (nitrogen, helium or argon).

For carrying out the process 2 according to the invention, in general from 0.5 to 4.0 mol, preferably from 0.7 to 3.0 mol, particularly preferably from 1.0 to 2.0 mol of alkylating agent of the formula (IV) are employed per mole of the compound of the formula (II).

After the reaction has gone to completion, the entire reaction mixture is concentrated. The products obtained after work-up can be purified in a customary manner by recrystallization, distillation under reduced pressure or column chromatography (cf. also the Preparation Examples).

If, in the process 3 according to the invention for preparing the novel compounds of the formula (I), in a first reaction step, the compound of the formula (II) used is, for example, tetronic acid and the compound of the formula (V) is 2-fluoroethylamine, and, in a second reaction step, the resulting compound of the formula (VI) is 4-[(2-fluoroethyl)amino)furan-2(5H)-one, which is N-alkylated with compounds of the formula (VII), for example 2-chloro-5-(chloromethyl) pyridin, the preparation process 3 can be represented by reaction scheme V below:

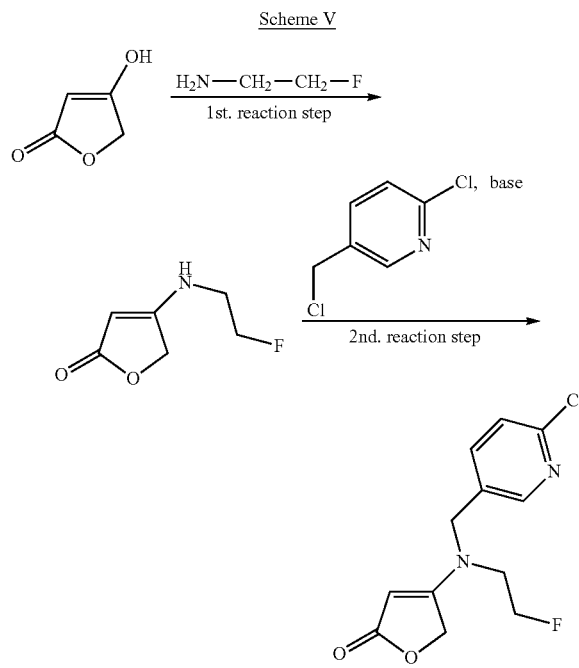

The formula (II) provides a general definition of the compounds required as starting materials for carrying out the process 3 according to the invention and that have already been described in more detail in connection with process 1, mentioned further above.

The formula (V) provides a general definition of the compounds further to be used as starting materials for carrying out the process 3 according to the invention.

In formula (V), $R^1$ has the meaning already mentioned in connection with the description of the compounds of the formula (I) according to the invention.

The amino compounds of the formula (V) are defined in a general manner, and in many cases some of them are commercially available (cf., for example, 2-fluoroethylamine or 2,2-difluoroethylamine) or they can be obtained in a manner known per se by the Leuckart-Wallach reaction (for example 2-fluoroethylamine: U.S. Pat. No. 4,030,994 (1977); compounds of the formula (V) in which $R^1$ represents alkyl, primary amines: cf., for example, Houben-Weyl, Methoden der Organischen Chemie, Vol. XI/1, 4th. Ed. 1957, Georg. Thieme Verlag, Stuttgart, p. 648; M. L. Moore in "The Leuckart Reaction" in: Organic Reactions, Vol. 5, 2nd. Ed. 1952, New York, John Wiley & Sons, Inc. London) (cf., for example, also 3-fluoro-n-propylamine: U.S. Pat. No. 6,252, 087 B1; 3,3-difluoroprop-2-enylamine hydrochloride: WO 2001/007414 A1; 3,3-dichloroprop-2-enylamine: DE 2747814); 2-chloro-2-fluorocyclopropylamine, 2,2-dichlorocyclopropylamine: K. R. Gassen, B. Baasner, J. Fluorine Chem. 49, 127-139, 1990).

Alternatively, certain amino compounds of the formula (Va) in which $R^1$ represents $CH_2$—R' (R'=halogen-containing radical; halogen=fluorine or chlorine) can also be obtained by reduction of halogenated carboxamides (VIII) in the presence of suitable reducing agents (reaction scheme VI).

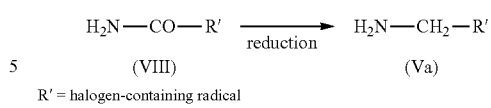

R' = halogen-containing radical

A preferred reducing agent is, for example, the known borane-dimethyl sulphide complex (cf. also the preparation of 2-chloro-2-fluoroethane-1-amine from commercially available 2-chloro-2-fluoroacetamide).

The formula (VII) provides a general definition of the compounds further to be used as starting materials for carrying out the process 3 according to the invention.

In the formula (VII), E and A have the meaning already mentioned in connection with the description of the compounds of the formula (I) according to the invention.

As already mentioned further above, some of the compounds of the general formula (VII) are commercially available, some are known or they can be obtained by known methods.

In general, it is advantageous to carry out the first reaction step of the preparation process 3 according to the invention in the presence of diluents. Diluents are advantageously employed in such an amount that the reaction mixture remains readily stirrable during the entire process. Suitable diluents for carrying out the process 3 according to the invention are all inert organic solvents.

Preferred diluents for carrying out the first reaction step of the process 3 according to the invention are aromatic hydrocarbons, such as benzene, toluene, chlorobenzene, bromobenzene, nitrobenzene or xylene, in particular benzene and toluene.

In the second reaction step, the compounds of the formula (VI) are N-alkylated with compounds of the formula (VII).

In general, it is advantageous to carry out the second reaction step of the preparation process 3 according to the invention in the presence of diluents and in the presence of basic reaction auxiliaries such as, for example, sodium hydride.

Suitable diluents for this reaction step are, for example, ethers, such as tetrahydrofuran or dioxane.

Diluents are advantageously employed in such an amount that the reaction mixture remains readily stirrable during the entire process.

The reaction time is generally from 10 minutes to 48 hours.

The reaction is carried out at temperatures between −10° C. and +200° C., preferably between +10° C. and 180° C., particularly preferably between 60° C. and 140° C. The reaction is preferably carried out under reaction conditions which allow water to be separated off or to be removed, for example with the aid of a water separator.

After the reaction has gone to completion, the entire reaction mixture is concentrated. The products obtained after work-up can be purified in a customary manner by recrystallization, distillation under reduced pressure or column chromatography (cf. also the Preparation Examples).

To prepare the compounds of the formula (I) in which $R^2$ represents a 2-fluorovinyl radical, according to the invention compounds of the formula (I) in which $R^2$ represents a 2-chloro-2-fluoroethyl radical are dehydrohalogenated (i.e. subjected to a formal elimination of HCl) in the presence of a basic auxiliary, according to reaction scheme (VII). The reaction products can be present in the form of geometrical isomers, for example (E) and (Z) isomers (or trans and cis isomers).

Scheme VII

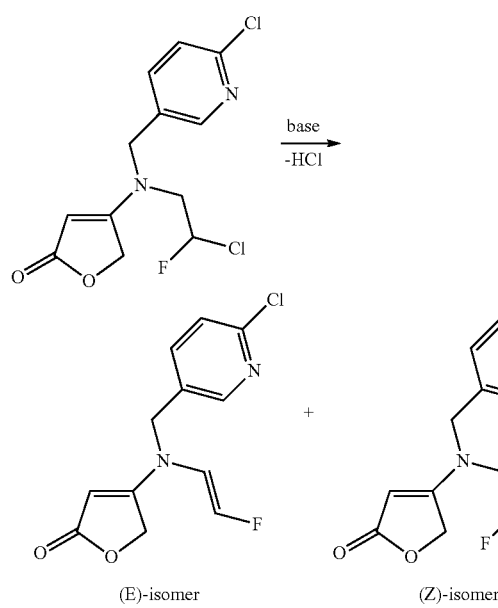

(E)-isomer     (Z)-isomer

In the compounds of the formula (I), required as starting materials for the dehydrohalogenation, A, B, $R^2$ and $R^3$ are as defined further above, the substituent $R^1$ has the meaning 2-chloro-2-fluoroethyl.

These compounds of the formula (I) can be obtained by the preparation processes 1 to 3 mentioned further above.

In general, it is advantageous to carry out the dehydrohalogenation in the presence of diluents. Diluents are advantageously employed in such an amount that the reaction mixture remains readily stirrable during the entire process. Suitable diluents for carrying out the C-alkylation are all organis solvents which are inert under the reaction conditions.

Preferred diluents for carrying out the dehydrohalogenation are alcohols, such as methanol, ethanol, isopropanol, butanol. It is also possible to use mixtures of the solvents and diluents mentioned for the process according to the invention.

Preferred diluents for carrying out the process according to the invention are alcohols, such as ethanol or butanol.

The dehydrohalogenation of compounds of the formula (I) is carried out by reacting them with compounds of the general formula (I) in the presence of basic reaction auxiliaries.

In general, the basic reaction auxiliaries used are advantageously alkali metal hydroxides, such as, for example, sodium hydroxide or potassium hydroxide.

The reaction time is generally from 10 minutes to 48 hours.

The reaction is carried out at temperatures between −100° C. and +80° C., preferably between −20° C. and 50° C., particularly preferably at room temperature.

After the reaction has gone to completion, the entire reaction mixture is concentrated. The products obtained after work-up can be purified in a customary manner by recrystallization, distillation under reduced pressure or column chromatography. The geometrical isomers, for example the (E) and (Z) isomers, are detected using known analytical methods. In the above-mentioned example, for example, an (E/Z) isomer mixture in a ratio of (15:85) is present (cf. also the Preparation Examples).

To prepare the compounds of the formula (I) in which $R^3$ represents alkyl, according to the invention compounds of the formula (I) in which $R^3$ represents hydrogen are reacted with compounds of the formula (IV) in the presence of basic auxiliaries, according to reaction scheme (VIII).

Scheme VIII

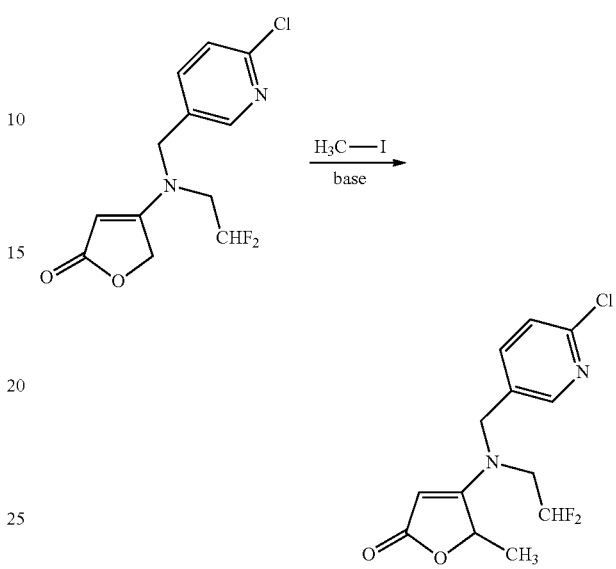

In the compounds of the formula (I), required as starting materials for the C-alkylation, A, B, $R^2$ and $R^3$ are as defined further above, the substituent $R^1$ represents hydrogen.

These compounds of the formula (I) can be obtained by the preparation processes 1 to 3 mentioned further above.

In general, it is advantageous to carry out the C-alkylation in the presence of diluents. Diluents are advantageously employed in such an amount that the reaction mixture remains readily stirrable during the entire process. Suitable diluents for carrying out the C-alkylation are all inert organic solvents.

Preferred diluents for carrying out the C-alkylation are ethers, such as methyl tert-butyl ether, n-butyl ether, anisole, phenetole, cyclohexyl methyl ether, diisopropyl ether, diisobutyl ether, diisoamyl ether, ethylene glycol dimethyl ether, tetrahydrofuran, dioxane, dichlorodiethyl ether and polyethers of ethylene oxide and/or propylene oxide.

It is also possible to use mixtures of the solvents and diluents mentioned for the process according to the invention.

Preferred diluents for carrying out the process according to the invention are ethers, such as methyl tert-butyl ether or cyclic ethers, such as tetrahydrofuran and dioxane.

The C-alkylation is carried out by reacting suitable starting materials of the formula I with compounds of the formula (IV) in the presence of basic reaction auxiliaries.

The reaction time is generally from 10 minutes to 48 hours.

The reaction is carried out at temperatures between −100° C. and +20° C., preferably between −90° C. and 10° C., particularly preferably between −80° C. and 0° C.

After the reaction has gone to completion, the entire reaction mixture is concentrated. The products obtained after work-up can be purified in a customary manner by recrystallization, distillation under reduced pressure or column chromatography (cf. also the Preparation Examples).

To prepare the compounds of the formula (I) in which $R^2$ represents halogen, it is alternatively also possible to react compounds of the formula (I) in which $R^2$ represents hydrogen with halogenating agents in the presence of basic auxiliaries, according to reaction scheme (IX).

Scheme IX:

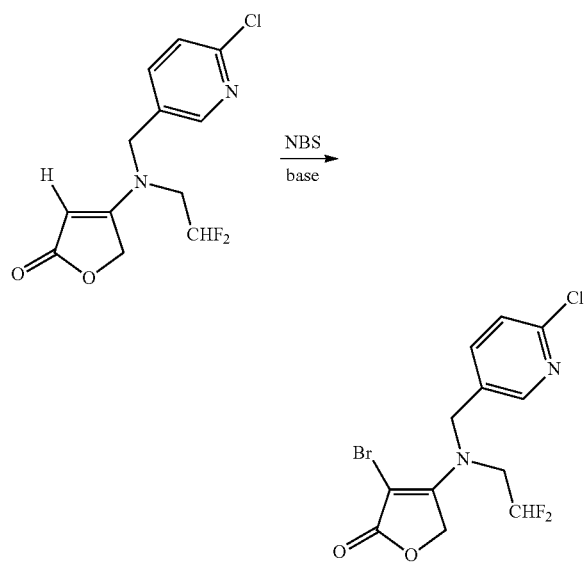

NBS: N-bromosuccinimide

In the compounds of the formula (I) required as starting materials, A, B, $R^1$ and $R^3$ are as defined further above, the substituent Rz represents hydrogen.

These compounds of the formula (I) can be obtained by the preparation processes 1 to 3 mentioned further above.

In general, it is advantageous to carry out the halogenation in the presence of diluents. Diluents are advantageously employed in such an amount that the reaction mixture remains readily stirrable during the entire process. Suitable diluents for carrying out the halogenation are all organic solvents which are inert under the reaction conditions.

Suitable halogenating agents for carrying out the process according to the invention are all suitable halogenating agents, for example N-halo compounds.

Examples which may be mentioned are N-haloamines, such as 1-chloromethyl-4-fluorodiazoniabicyclo[2.2.2]octan-bis-(tetrafluoroborate) (Selectfluor®), N,N-dihaloamines, N-halocarboxamides, N-halocarbamidic acid esters, N-halourea, N-halosulphonylamides, N-halodisulphonylamides, N-halosulphonylimides, such as N-fluorobis[(trifluoromethyl)sulphonyl]imide, and N-halocarboxylic acid diamides, such as N-chlorophthalimide, N-bromophthalimide, N-iodophthalimide, N-chlorosuccinimide (NCS), N-bromosuccinimide (NBS), N-bromosaccharin or N-iodosuccinimide.

Preferred halogenating agents for carrying out the halogenation are N-halocarboxylic acid diamides or 1-chloromethyl-4-fluorodiazoniabicyclo[2.2.2]octane-bis-(tetrafluoroborate) (Selectfluor®).

Preferred diluents for carrying out the halogenation are nitriles, such as acetonitrile, propionitrile, butyronitrile, isobutyronitrile, benzonitrile, m-chlorobenzonitrile.

It is also possible to use mixtures of the solvents and diluents mentioned for the process according to the invention.

Particularly preferred diluents for carrying out the process according to the invention are nitriles, such as acetonitrile, propionitrile or butyronitrile.

The reaction time in this process is generally from 10 minutes to 48 hours.

The reaction is carried out at temperatures between −10° C. and +100° C., preferably between 0° C. and 60° C., particularly preferably between 10° C. and room temperature.

After the reaction has gone to completion, the entire reaction mixture is concentrated. The products obtained after work-up can be purified in a customary manner by recrystallization, distillation under reduced pressure or column chromatography (cf. also the Preparation Examples).

If appropriate, the compounds of the formula (I) can be present in different polymorphic forms or as a mixture of different polymorphic forms. Both the pure polymorphs and the polymorph mixtures are provided by the invention and can be used according to the invention.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as Eimeria.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp, *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofinannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americava*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkyl aryl and/or POP-POE ethers, fat and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

Particularly favourable mixing components are, for example, the following compounds:

Fungicides:

Inhibitors of Nucleic Acid Synthesis
  benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid Inhibitors of Mitosis and Cell Division
  benomyl, carbendazim, diethofencarb, fuberidazole, pencycuron, thiabendazole, thiophanatmethyl, zoxamide Inhibitors of Respiratory Chain Complex I
  diflumetorim Inhibitors of Respiratory Chain Complex II
  boscalid, carboxin, fenfuram, flutolanil, furametpyr, mepronil, oxycarboxin, penthiopyrad, thifluzamide Inhibitors of Respiratory Chain Complex III
  azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin Decouplers
   dinocap, fluazinam
Inhibitors of ATP Production
   fentin acetate, fentin chloride, fentin hydroxide, silthiofam
Inhibitors of Amino Acid Biosynthesis and Protein Biosynthesis
   andoprim, blasticidin-S, cyprodinil, kasugamycin, kasugamycin hydrochloride hydrate, mepanipyrim, pyrimethanil
Inhibitors of Signal Transduction
   fenpiclonil, fludioxonil, quinoxyfen
Inhibitors of Lipid and Membrane Synthesis
   chlozolinate, iprodione, procymidone, vinclozolin
   ampropylfos, potassium-ampropylfos, edifenphos, iprobenfos (IBP), isoprothiolane, pyrazophos
   tolclofos-methyl, biphenyl
   iodocarb, propamocarb, propamocarb hydrochloride
Inhibitors of Ergosterol Biosynthesis
   fenhexamid,
   azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidole, nuarimol, pyrifenox, triforine, pefurazoate, prochloraz, triflumizole, viniconazole,
   aldimorph, dodemorph, dodemorph acetate, fenpropimorph, tridemorph, fenpropidin, spiroxamine,
   naftifine, pyributicarb, terbinafine
Inhibitors of Cell Wall Synthesis
   benthiavalicarb, bialaphos, dimethomorph, flumorph, iprovalicarb, polyoxins, polyoxorim, validamycin A
Inhibitors of Melanin Biosynthesis
   capropamid, diclocymet, fenoxanil, phthalid, pyroquilon, tricyclazole
Resistance Inductors
   acibenzolar-S-methyl, probenazole, tiadinil
Multisite
   captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram
Unknown Mechanism
   amibromdol, benthiazol, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulphamide, fluopicolide, fluoroimide, hexachlorobenzene, 8-hydroxyquinoline sulphate, irumamycin, methasulphocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrol nitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzenesulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethyl-isoxazolidin-3-yl]pyridine, cis-1-(4-chlorophenyl)-2-(1H-1,2,4-triazol-1-yl) cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alphapropynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulphonyl)amino]butanamide, 5-chloro-7-(4-methylpiperidin-1-yl)-6-(2,4,6-trifluorophenyl)[1,2,4]-triazolo[1,5-a]pyrimidine, 5-chloro-6-(2,4,6-trifluorophenyl)-N-[(1R)-1,2,2-trimethylpropyl]-[1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaEbenzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide Bactericides:
   bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
Acetylcholine Esterase (AChE) Inhibitors
   carbamates,
   for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulphan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
   organophosphates,
   for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulphoton, EPN, ethion, ethoprophos, etrimfos, famphur, fenamiphos, fenitrothion, fensulphothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulphotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers
- pyrethroids,
  - for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum)
- DDT
- oxadiazines,
  - for example indoxacarb
- semicarbazones,
  - for example metaflumizone (BAS3201)

Acetylcholine Receptor Agonists/Antagonists
- chloronicotinyls,
  - for example acetamiprid, clothianidin, dinotefuran, imidacloprid, nitenpyram, nithiazine, thiacloprid, imidaclothiz, AKD-1022, thiamethoxam
- nicotine, bensultap, cartap Acetylcholine Receptor Modulators
- spinosyns,
  - for example spinosad, spinetoram (XDE-175)

GABA-Controlled Chloride Channel Antagonists
- organochlorines,
  - for example camphechlor, chlordane, endosulphan, gamma-HCH, HCH, heptachlor, lindane, methoxychlor
- fiprols,
  - for example acetoprole, ethiprole, fipronil, pyrafluprole, pyriprole, vaniliprole Chloride Channel Activators
- mectins,
  - for example abarmectin, emamectin, emamectin-benzoate, ivermectin, lepimectin, milbemycin Juvenile Hormone Mimetics,
- for example diofenolan, epofenonane, fenoxycarb, hydroprene, kinoprene, methoprene, pyriproxifen, triprene Ecdysone Agonists/Disruptors
- diacylhydrazines,
  - for example chromafenozide, halofenozide, methoxyfenozide, tebufenozide Chitin Biosynthesis Inhibitors
- benzoylureas,
  - for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
- buprofezin
- cyromazine Oxidative Phosphorylation Inhibitors, ATP Disruptors
- diafenthiuron
- organotin compounds,
  - for example azocyclotin, cyhexatin, fenbutatin-oxide Oxidative Phosphorylation Decouplers Acting by Interrupting the H-Proton Gradient
- pyrroles,
  - for example chlorfenapyr
- dinitrophenols,
  - for example binapacyrl, dinobuton, dinocap, DNOC Site-I Electron Transport Inhibitors
- METIs,
  - for example fenazaquin, fenpyroximate, pyrimidifen, pyridaben, tebufenpyrad, tolfenpyrad hydramethylnon
- dicofol Site-II Electron Transport Inhibitors
- rotenone Site-III Electron Transport Inhibitors
- acequinocyl, fluacrypyrim Microbial Disruptors of the Insect Gut Membrane
- *Bacillus thuringiensis* strains Lipid Synthesis Inhibitors
- tetronic acids,
  - for example spirodiclofen, spiromesifen
- tetramic acids,
  - for example spirotetramat
- carboxamides,
  - for example flonicamid
- octopaminergic agonists,
  - for example amitraz Inhibitors of Magnesium-Stimulated ATPase,
- propargite
- nereistoxin analogues,
  - for example thiocyclam hydrogen oxalate, thiosultap-sodium Ryanodin Receptor Agonists
- benzoic acid dicarboxamides,
  - for example flubendiamid
- anthronilamides,
  - for example pynaxypyr (3-bromo-N-{4-chloro-2-methyl-6-[(methylamino)carbonyl]phenyl}-1-(3-chloropyridin-2-yl)-1H-pyrazole-5-carboxamide)

Biologicals, Hormones or Pheromones
- azadirachtin, *Bacillus* spec., *Beauveria* spec., codlemone, *Metarrhizium* spec., *Paecilomyces* spec., thuringiensin, *Verticillium* spec.

Active Compounds with Unknown or Unspecific Mechanisms of Action
- fumigants,
  - for example aluminium phosphide, methyl bromide, sulphuryl fluoride
- antifeedants,
  - for example cryolite, flonicamid, pymetrozine
- mite growth inhibitors,
  - for example clofentezine, etoxazole, hexythiazox amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulphluramid, tetradifon, tetrasul, triarathene, verbutin A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

Treatment according to the invention of the plants and plant parts with the active compound combinations is carried out directly or by allowing the compounds to act on the surroundings, habitat or storage space by the customary treatment methods, for example by immersion, spraying, evaporation, fogging, scattering, painting on, and, in the case of propagation material, in particular in the case of seeds, also by applying one or more coats.

The mixtures according to the invention are particularly suitable for treating seed. Here, the combinations according to the invention mentioned above as preferred or particularly preferred may be mentioned as being preferred. Thus, a large part of the damage to crop plants which is caused by pests occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seeds of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection agents being employed.

The present invention therefore in particular also relates to a method for the protection of seed and germinating plants from attack by pests, by treating the seed with a composition according to the invention. The invention likewise relates to the use of the compositions according to the invention for the treatment of seed for protecting the seed and the resultant plant from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plants after emergence, from pests. In this manner, the immediate treatment of the crop at the time of sowing or shortly thereafter can be dispensed with.

A further advantage is the synergistically increased insecticidal activity of the compositions according to the invention in comparison with the individual insecticidal active compound, which exceeds the anticipated activity of the two active compounds when applied individually. Also advantageous is the synergistically increased fungicidal activity of the compositions according to the invention in comparison with the individual fungicidal active compound, which exceeds the anticipated activity of the active compound when applied individually. This makes possible an optimization of the amount of active compound employed.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and additionally be protected by the compositions according to the invention against damage.

The compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage plants). The compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with a composition according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene orignating from *Bacillus* sp. and whose gene product shows activity against the European corn borer and/or the corn root worm. It is particularly preferably a heterologous gene derived from *Bacillus thuringiensis*.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetis engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., Notoedres spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with seawater or brackish water, such as hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

PREPARATION EXAMPLES

Process 1

Variant A

4-[[(6-Chloropyridin-3-yl)methyl](2,2-difluoroethyl)amino]furan-2(5H)-one

Example (1)

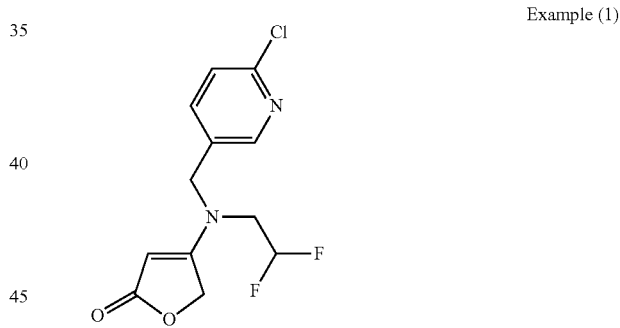

On a water separator, 21.90 g (106.0 mmol) of N-[(6-chloropyridin-3-yl)methyl]-2,2-difluoroethane-1-amine (III-1), 14.85 g (148.4 mmol) of tetronic acid and 183 mg (1.1 mmol) of 4-toluenesulphonic acid in 250 ml of toluene are heated under reflux for 2 hours. The reaction mixture is concentrated under reduced pressure, the residue is then taken up in ethyl acetate and the mixture is washed successively twice with 1 N aqueous hydrochloric acid, twice with 1 N aqueous sodium hydroxide solution and once with saturated sodium chloride solution. The organic phase is dried over sodium sulphate and concentrated under reduced pressure. Purification of the residue by column chromatography on silica gel (silica gel 60—Merck, particle size: 0.04 to 0.063 mm) using the mobile phase ethyl acetate gives 15.9 g (52% of theory) of 4-[[(6-chloropyridin-3-yl)methyl](2,2-difluoroethyl)amino]furan-2(5H)-one.

$^1$H-NMR (CD$_3$CN, δ, ppm)=3.59 (td, 2H), 4.51 (s, 2H), 4.76 (s, 1H), 4.80 (s, 2H), 6.03 (tt, 1H), 7.38 (d, 1H), 7.64 (dd, 1H), 8.28 (d, 1H).

Variant B

4-[[(6-Chloropyridin-3-yl)methyl](3-fluoro-n-propyl)amino]furan-2(5H)-one

Example (2)

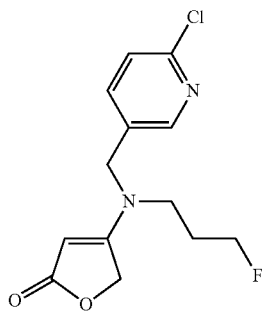

0.52 g (5.18 mmol) of tetronic acid is initially charged in 1.13 ml of acetic acid, and 1.00 g (4.93 mmol) of N-[(6-chloropyridin-3-yl)methyl]-3-fluoropropane-1-amine (III-2) is added slowly at room temperature. The entire reaction mixture is then stirred at room temperature for approximately a further 18 hours. The reaction mixture is concentrated under reduced pressure, the residue is then taken up in dichloromethane and the mixture is washed with water. After phase separation, the aqueous phase is extracted twice with dichloromethane. The combined organic phases are then made alkaline (pH>9) with 1 N sodium hydroxide solution and the phases are separated. The aqueous phase is extracted twice with dichloromethane, and, after phase separation, the combined organic phases are dried over sodium sulphate. Concentration of the organic phase under reduced pressure and purification of the residue by column chromatography on silica gel (silica gel 60-Merck, particle size: 0.04 to 0.063 mm) using the mobile phase mixture ethyl acetate:cyclohexane (9:1) gives 191 mg (14% of theory) of 4-[[(6-chloropyridin-3-yl)methyl](3-fluoro-npropyl)amino]furan-2(5H)-one.

$^1$H-NMR (CD$_3$CN, δ, ppm)=1.95 (m, 2H), 3.30 (t, 2H), 4.40 (s, 2H), 4.45 (dt, 2H), 4.65 (s, 1H), 4.80 (s, 2H), 7.40 (d, 1H), 7.65 (dd, 1H), 8.28 (d, 1H).

The compounds (16) and (17) were also prepared analogously to this procedure.

Process 2

4-[[(6-Chloropyridin-3-yl)methyl](3,3-dichloroprop-2-en-1-yl)amino]furan-2(5H)-one Example (3)

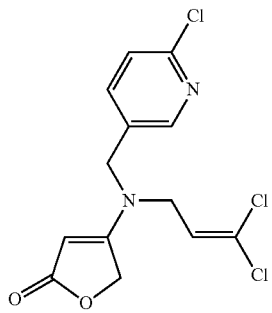

350 mg (1.56 mmol) of 4-[[(6-chloropyridin-3-yl)methyl]amino]furan-2(5H)-one (Ia-1; cf. EP 0539588 A 1) and 124 mg (3.12 mmol) of a 60% dispersion of sodium hydride in mineral oil in 100 ml of tetrahydrofuran are heated under reflux for 3 h. After cooling to room temperature, 592 mg (3.12 mmol) of 3-bromo-1,1-dichloroprop-1-ene (cf. WO 8800183A1) are added and the mixture is heated under reflux for a further 5 h. After cooling of the reaction mixture to room temperature and addition of methanol, the mixture is concentrated under reduced pressure. The residue is taken up in ethyl acetate and the mixture is washed successively twice with 1 N aqueous hydrochloric acid, twice with 1 N aqueous sodium hydroxide solution and once with saturated sodium chloride solution. The organic phase is then dried over sodium sulphate and concentrated under reduced pressure. Purification of the residue by column chromatography on silica gel (silica gel 60—Merck, particle size: 0.04 to 0.063 mm) using the mobile phase mixture ethyl acetate: cyclohexane (2:1) gives 264 mg (50% of theory) of 4-[[(6-chloropyridin-3-yl)methyl](3,3-dichloroprop-2-en-1-yl)amino]furan-2(5H)-one.

$^1$H-NMR (CD$_3$CN, δ, ppm)=3.90 (d, 2H), 4.38 (s, 2H), 4.71 (s, 1H), 4.80 (s, 2H), 6.02 (t, 1H), 7.38 (d, 1H), 7.66 (dd, 1H), 8.29 (d, 1H).

The compounds (9) and (12) were also prepared analogously to this procedure.

Process 3

4-[[(6-Chloropyridin-3-yl)methyl](2-fluoroethyl)amino]furan-2(5H)-one

Example (4)

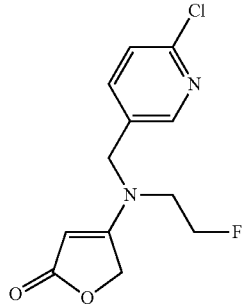

1.00 g (6.89 mmol) of 4-[(2-fluoroethyl)amino]furan-2(5H)-one (VI-1) and 0.55 g (13.78 mmol) of a 60% dispersion of sodium hydride in mineral oil in 200 ml of tetrahydrofuran are heated under reflux for 2 h. After cooling to room temperature, 2.23 g (13.78 mmol) of 2-chloro-5-chloromethylpyridine are added, and the mixture is heated under reflux for a further 4 hours. The reaction mixture is cooled to room temperature, and methanol is added. After concentration of the reaction mixture under reduced pressure, the residue is taken up in ethyl acetate and the mixture is washed successively twice with 1 N aqueous hydrochloric acid, twice with 1 N aqueous sodium hydroxide solution and once with saturated sodium chloride solution. The organic phase is then dried over sodium sulphate and concentrated under reduced pressure. Purification of the residue by column chromatography on silica gel (silica gel 60—Merck, particle size: 0.04 to 0.063 mm) using the mobile phase mixture ethyl acetate:cyclohexane (9:1) gives 949 mg (50% of theory) of 4-[[(6-chloropyridin-3-yl)methyl](2-fluoroethyl)amino]furan-2(5H)-one.

$^1$H-NMR (CD$_3$CN, δ, ppm)=3.50 (dt, 2H), 4.50 (s, 2H), 4.57 (dt, 2H), 4.65 (s, 1H), 4.79 (s, 2 H), 7.38 (d, 1H), 7.65 (dd, 1H), 8.28 (d, 1H).

The compounds (10), (11), (13), (14) and (15) were also prepared analogously to this procedure.

(E/Z)-4-[[(6-Chloropyridin-3-yl)methyl](2-fluorovinyl)amino]-5-methylfuran-2(5H)-one Example (5)

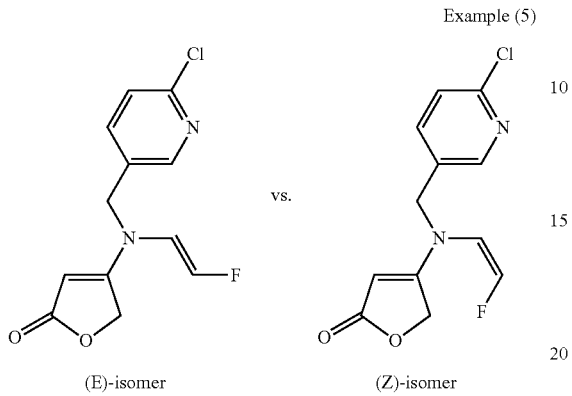

(E)-isomer vs. (Z)-isomer 68 mg (0.22 mmol) of 4-[[(6-chloropyridin-3-yl)methyl](2-chloro-2-fluoroethyl)amino]furan-2(5H)-one (17) are initially charged in 5 ml of ethanol, 38 mg (0.67 mmol) of potassium hydroxide are added and the reaction mixture is stirred at room temperature for about 18 hours. The reaction mixture is then partitioned between ethyl acetate and water, and the organic phase is separated off. The organic phase is washed with saturated sodium chloride solution, dried over sodium sulphate and concentrated under reduced pressure. Purification of the residue by column chromatography on silica gel (silica gel 60—Merck, particle size: 0.04 to 0.063 mm) using the mobile phase mixture ethyl acetate:cyclohexane (2:1) gives 57 mg (94% of theory) of 4-[[(6-chloropyridin-3-yl)methyl](2-fluorovinyl)amino]-5-methylfuran-2(5H)-one as an (E/Z) isomer mixture (15:85).

$^1$H-NMR (CD$_3$CN, δ, ppm)=4.75 (s, 2H), 4.84 (s, 2H), 4.88 (s, 1H), 5.60 (dd, 1H), 6.37 (dd, 1H), 7.39 (d, 1H), 7.67 (dd, 1H), 8.29 (d, 1H) [(Z) isomer; 85% according to NMR].

$^1$H-NMR (CD$_3$CN, δ, ppm)=6.90 (dd, 1H) [(E) isomer; 15% according to NMR].

4-[[(6-Chloropyridin-3-yl)methyl](2,2-difluoroethyl)amino]-5-methylfuran-2(5H)-one Example (6)

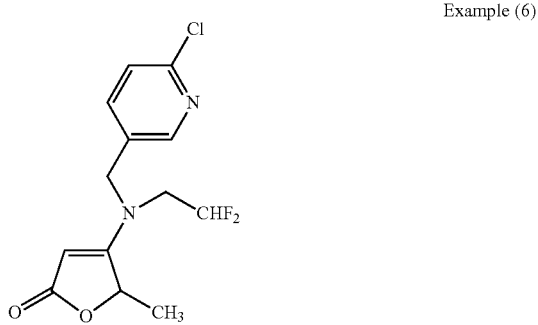 [SMILES: CC1OC(=O)C=C1N(Cc1ccc(Cl)nc1)CC(F)F]

300 mg (1.04 mmol) of 4-[[(6-chloropyridin-3-yl)methyl](2,2-difluoroethyl)amino]furan-2(5H)one (1) are dissolved in 10 ml of tetrahydrofuran, the solution is cooled to −78° C. and 611 µl (1.04 mmol) of a 1.7 M solution of tert.-butyllithium in pentane are added. After 30 min of stirring at −78° C., 65 µl (1.04 mmol) of methyl iodide are added, stirring is continued at −78° C. for a further 30 min and the mixture is warmed to room temperature. Concentration under reduced pressure and purification of the residue by column chromatography on silica gel (silica gel 60—Merck, particle size: 0.04 to 0.063 mm) using the mobile phase mixture ethyl acetate:cyclohexane (2:1) gives 152 mg (47% of theory) of 4-[[(6-chloropyridin-3-yl)methyl](2,2-difluoroethyl)amino]-5-methylfuran-2(5H)-one.

$^1$H-NMR (CD$_3$CN, δ ppm)=1.48 (d, 3H), 3.59 (m, 2H), 4.48 (d, 1H), 4.58 (d, 1H), 4.73 (s, 1 H), 5.10 (q, 1H), 6.06 (tt, 1H), 7.40 (d, 1H), 7.65 (dd, 1H), 8.28 (d, 1H).

3-Bromo-4-[[(6-chloropyridin-3-yl)methyl](2,2-difluoroethyl)amino]furan-2(5H)-one Example (7)

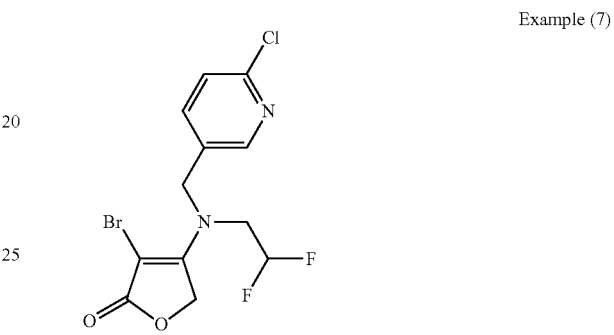

313 mg (1.08 mmol) of 4-[[(6-chloropyridin-3-yl)methyl](2,2-difluoroethyl)amino]furan-2(5H)one (1) are dissolved in 20 ml of acetonitrile, and 166 µl (1.19 mmol) of triethylamine and 386 mg (2.17 mmol) of N-bromosuccinimide are added at room temperature. After 3 hours of stirring, the mixture is concentrated under reduced pressure. Purification of the residue by column chromatography on silica gel (silica gel 60—Merck, particle size: 0.04 to 0.063 mm) using the mobile phase mixture ethyl acetate:cyclohexane (2:1) gives 312 mg (63% of theory) of 3-bromo-4-[[(6-chloropyridin-3-yl)methyl](2,2-difluoroethyl)amino]furan-2(5H)-one.

$^1$H-NMR (CD$_3$CN, δ, ppm)=3.80 (td, 2H), 4.83 (s, 2H), 4.85 (s, 2H), 6.08 (tt, 1H), 7.40 (d, 1 H), 7.66 (dd, 1H), 8.30 (d, 1H).

3-Chloro-4-[[(6-chloropyridin-3-yl)methyl](2,2-difluoroethyl)amino]furan-2(5H)-one Example (8)

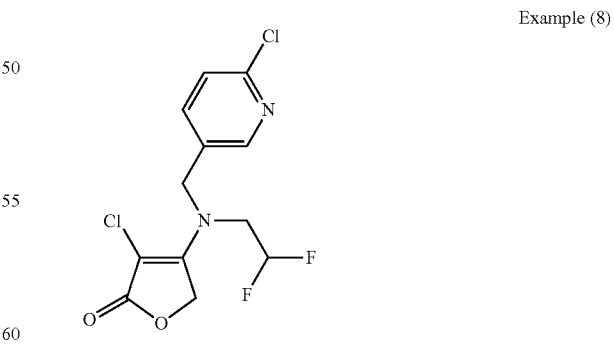

The halogenation reaction is carried out analogously to the reaction procedure of Example 6 using: 329 mg (1.14 mmol) of 4-[[(6-chloropyridin-3-yl)methyl](2,2-difluoroethyl)amino]furan-2(5H)one (1)
0.17 ml (1.25 mmol) of triethylamine
304 mg (2.28 mmol) of N-chlorosuccinimide 20 ml of acetonitrile The residue that remains is purified by column chromatography on silica gel (silica gel 60—Merck, particle size: 0.04 to 0.063 mm) using the mobile phase mixture ethyl acetate: cyclohexane (2:1). This gives 292 mg (63% of theory) of 3-chloro-4-[[(6-chloropyridin-3-yl)methyl](2,2-difluoroethyl)amino]furan-2(5H)-one.

$^1$H-NMR (CD$_3$CN, δ ppm)=3.79 (td, 2H), 4.78 (s, 2H), 4.82 (s, 2H), 6.07 (tt, 1H), 7.40 (d, 1H), 7.67 (dd, 1H), 8.30 (d, 1H).

Further compounds (9) to (17) of the formula (I) are listed in Table 1 below.

TABLE 1

Compounds of the formula (I)

| Ex. No. | A | B | R$^1$ | R$^2$ | R$^3$ | Physical Data: $^1$H-NMR, δ [ppm] |
|---|---|---|---|---|---|---|
| 9 | 5-methyl-2-chloropyridin-3-yl | O | CH$_2$CHF$_2$ (isopropyl-type, 2F) | H | H | CD$_3$Cl, δ = 4.62 (s, 2H), 4.93 (s, 2H), 5.00 (s, 1H), 6.50 (t, 1H), 7.38 (d, 1H), 7.57 (dd, 1H), 8.35 (d, 1H) |
| 10 | 5-methyl-2-chlorothiazol-4-yl | O | CH$_2$CH$_2$CH$_2$F | H | H | CD$_3$CN, δ = 3.48 (dt, 2H), 4.57 (dt, 2H), 4.58 (s, 2H), 4.71 (s, 1H), 4.78 (s, 2H), 7.50 (s, 1H) |
| 11 | 5-methyl-2-bromopyridin-3-yl | O | CH$_2$CH$_2$CH$_2$F | H | H | CD$_3$CN, δ = 3.50 (dt, 2H), 4.47 (s, 2H), 4.55 (dt, 2H), 4.65 (s, 1H), 4.80 (s, 2H), 7.53 (s, 2H), 8.28 (s, 1H) |
| 12 | 5-methyl-2-chloropyridin-3-yl | O | CH$_2$CH=CF$_2$ | H | H | CD$_3$CN, δ = 3.78 (dm, 2H), 4.39 (s, 2H), 4.50 (dtd, 1H), 4.68 (s, 1H), 4.80 (s, 2H), 7.38 (d, 1H), 7.65 (dd, 1H), 8.28 (d, 1H) |
| 13 | 5-methyl-2-bromopyridin-3-yl | O | CH$_2$CH$_2$CHF$_2$ | H | H | CD$_3$CN, δ = 3.58 (td, 2H), 4.50 (s, 2H), 4.75 (s, 1H), 4.80 (s, 2H), 6.05 (tt, 1H), 7.55 (s, 2H), 8.28 (s, 1H) |
| 14 | 5-methyl-2-trifluoromethylpyridin-3-yl | O | CH$_2$CH$_2$CHF$_2$ | H | H | CD$_3$CN, δ = 3.61 (td, 2H), 4.63 (s, 2H), 4.75 (s, 1H), 4.80 (s, 2H), 6.05 (tt, 1H), 7.75 (d, 1H), 7.85 (d, 1H), 8.62 (s, 1H) |
| 15 | 5-methyl-2-fluoropyridin-3-yl | O | CH$_2$CH$_2$CHF$_2$ | H | H | CD$_3$CN, δ = 3.58 (td, 2H), 4.52 (s, 2H), 4.76 (s, 1H), 4.81 (s, 2H), 6.03 (tt, 1H), 7.00 (dd, 1H), 7.78 (td, 1H), 8.10 (s, 1H) |
| 16 | 5-methyl-2-chloropyridin-3-yl | CH$_2$ | CH$_2$CH$_2$CHF$_2$ | H | H | CD$_3$CN, δ = 2.30 (m, 2H), 2.74 (m, 2H), 3.71 (td, 2H), 4.61 (s, 2H), 5.01 (s, 1H), 6.05 (tt, 1H), 7.40 (d, 1H), 7.62 (dd, 1H), 8.28 (d, 1H) |
| 17 | 5-methyl-2-chloropyridin-3-yl | O | CH$_2$CH$_2$CHFCl | H | H | CD$_3$CN, δ = 3.75 (m, 2H), 4.55 (s, 2H), 4.75 (s, 1H), 4.82 (s, 2H), 6.43 (ddd, 1H), 7.38 (d, 1H), 7.65 (dd, 1H), 8.28 (d, 1H) |

Preparation of Starting Materials
Compounds of the Formula (Ia)
Ia-1

4-[[(6-Chloropyridin-3-yl)methyl]amino]furan-2(5H)-one (cf. EP 0539588 A1)

On a water separator, 5.00 g (35.1 mmol) of 1-(6-chloropyridin-3-yl)methylamine, 3.51 g (35.1 mmol) of tetronic acid and 20 mg (0.12 mmol) of 4-toluenesulphonic acid in 200 ml of toluene are heated under reflux for 24 hours. The reaction mixture is concentrated, and the residue that remains is then purified by column chromatography on silica gel (silica gel 60—Merck, particle size: 0.04 to 0.063 mm) using the mobile phase ethyl acetate. This gives 4.96 g (63% of theory) of 4-[[(6-chloropyridin-3-yl)methyl]amino]furan-2(5H)-one, which can be used for subsequent reactions.

$^1$H-NMR (CDCl$_3$, δ ppm)=4.35 (d, 2H), 4.70 (s, 2H), 4.80 (s, 1H), 4.95 (br. s, 1H), 7.36 (d, 1H), 7.61 (dd, 1H), 8.37 (d, 1H).

Compounds of the Formula (III)
III-1

N-[(6-Chloropyridin-3-yl)methyl]-2,2-difluoroethane-1-amine 41.57 g (256.6 mmol) of 2-chloro-5-chloromethylpyridine, 20.80 g (256.6 mmol) of 2,2-difluoroethane-1-amine and 35.8 ml (256.6 mmol) of triethylamine in 500 ml of acetonitrile are stirred at 45° C. for 21 hours. The reaction mixture is concentrated under reduced pressure and the residue is then taken up in 1 N aqueous hydrochloric acid and the mixture is washed with ethyl acetate. The aqueous phase is made alkaline using 2.5 N aqueous sodium hydroxide solution and extracted repeatedly with ethyl acetate. Concentration of the organic phase under reduced pressure gives 28.6 g (53% of theory) of N-[(6-chloropyridin-3-yl)methyl]-2,2-difluoroethane-1-amine.

$^1$H-NMR (CD$_3$CN, δ, ppm)=2.93 (td, 2H), 3.80 (s, 2H), 5.85 (tt, 1H), 7.33 (d, 1H), 7.71 (dd, 1H), 8.30 (d, 1H).

The following compounds can be prepared analogously:
III-2

N-[(6-Chloropyridin-3-yl)methyl]-3-fluoropropane-1-amine

LCMS (m/z, %)=203 (MIT, 100).
III-3

N-[(6-Chloropyridin-3-yl)methyl]-2-chloro-2-fluoroethane-1-amine

LCMS (m/z, %)=223 (MH$^+$, 100).
Compounds of the Formula (V)
Va-1

2-Chlorofluoroethane-1-amine a) 5.00 g (44.8 mmol) of 2-chloro-2-fluoroacetamide are stirred in 50.0 ml of tetrahydrofuran, and 51.6 ml (103.1 mmol) of borane-dimethylsulphide complex are added dropwise. The reaction mixture is then stirred at reflux temperature for one hour. After cooling, 155.7 ml (0.45 mmol) of 10% strength hydrochloric acid are added carefully, and the mixture is stirred at reflux temperature for a further hour. The tetrahydrofuran is then removed under reduced pressure, the residue is cooled (ice bath) and stirred with diethyl ether and the mixture is adjusted to pH 9 using sodium hydroxide solution. The mixture is extracted three times with diethyl ether, and 44.8 ml (89.7 mmol) of hydrogen chloride in dioxane are added to the combined organic phase to form the hydrochloride. The precipitated hydrochloride is separated off and washed once more. This gives 3.48 g (58% of theory) of 2-chloro-3-fluoroethane-1-amine hydrochloride.

b) To form the free base, 2.03 g (50.8 mmol) of sodium hydroxide powder are added to 3.40 g (25.4 mmol) of 2-chloro-3-fluoroethane-1-amine hydrochloride (which is dried under high vacuum beforehand). The free base can then be distilled off at 100° C. This gives 2.10 g (85% of theory) of 2-chloro-3-fluoroethane-1-amine, which can be used for the synthesis of N-[(6-chloropyridin-3-yl)methyl]-2-chloro-2-fluoroethane-1-amine (III-3).

$^1$H-NMR (CD$_3$CN, δ ppm)=3.07 (dm, 2H), 6.17 (dt, 1H).
Compounds of the Formula (VI)
VI-1

4-[(2-Fluoroethyl)amino]furan-2(5H)-one

On a water separator, 550 mg (4.97 mmol) of 2-fluoroethylamine hydrochloride, 547 mg (5.47 mmol) of tetronic acid, 408 mg (4.97 mmol) of sodium acetate and 9 mg (0.05 mmol) of 4-toluenesulphonic acid in 50 ml of toluene are heated under reflux for 5 hours. The reaction mixture is concentrated under reduced pressure and then taken up in ethyl acetate and washed with 1 N aqueous sodium hydroxide solution. The aqueous phase is extracted repeatedly with ethyl acetate and the combined organic phase is dried over sodium sulphate. Concentration of the organic phase under reduced pressure and purification of the residue by recrystallization from ethyl acetate/cyclohexane gives 300 mg (42% of theory) of 4-[(2-fluoroethyl)amino]furan-2(5H)-one.

$^1$H-NMR (CD$_3$CN, δ, ppm)=3.40 (dq, 2H), 4.52 (dt, 2H), 4.61 (s, 1H), 4.62 (s, 2H), 5.80 (br. s, 1H).

The following compound can be prepared in an analogous manner:
VI-2

4-[(2,2-Difluoroethyl)amino]furan-2(5H)-one $^1$H-NMR (CD$_3$CN, δ, ppm)=3.50 (tm, 2H), 4.65 (s, 2H), 4.71 (s, 1H), 5.78 (br. s, 1H), 5.98 (tt, 1H).

BIOLOGICAL EXAMPLES

Example No. 1

*Myzus* Test (MYZUPE Spray Treatment)

| Solvent: | 78 parts by weight of acetone |
| --- | --- |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Disks of Chinese cabbage (*Brassica pekinensis*) which are infested with all stages of the green peach aphid (*Myzus persicae*) are sprayed with a preparation of active compound of the desired concentration.

After the desired period of time, the effect in % is determined. 100% means that all aphids have been killed; 0% means that none of the aphids have been killed. In this test, for example, the following compounds of the Preparation Examples show good activity: see table

| Example | Active compound concentration in g/ha | Kill rate in % after 5 days |
| --- | --- | --- |
| Example 3 | 500 | 100 |
| Example 12 | 500 | 100 |
| Example 10 | 500 | 100 |
| Example 11 | 500 | 100 |
| Example 14 | 500 | 100 |
| Example 13 | 500 | 100 |
| Example 15 | 500 | 100 |
| Example 2 | 500 | 100 |
| Example 7 | 500 | 100 |
| Example 8 | 500 | 100 |
| Example 6 | 500 | 100 |
| Example 17 | 500 | 100 |
| Example 5 | 500 | 100 |

Example No. 2

*Myzus* Test; Oral; (MYZUPE O)

| | |
| --- | --- |
| Solvent: | 80 parts by weight of acetone |

To produce a suitable preparation of active compound, 1 part by weight of active compound is mixed with the stated amounts of solvent, and the concentrate is diluted with water to the desired concentration.

Containers are populated with all stages of the green peach aphid (*Myzus persicae*), treatment is by sucking at the preparation of active compound of the desired concentration.

After the desired period of time, the effect in % is determined. 100% means that all aphids have been killed; 0% means that none of the aphids have been killed.

In this test, for example, the following compounds of the Preparation Examples show good activity: see table

| Example | Active compound concentration in ppm | Kill rate in % after 5 days |
| --- | --- | --- |
| Example 2 | 20 | 100 |

Example No. 3

*Nilaparvata lugens* Test (NILALU Hydroponic Treatment)

| | |
| --- | --- |
| Solvent: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

The preparation of active compound is pipetted into water. The stated concentration refers to the amount of active compound per volume unit of water (mg/l=ppm). The water is then infected with the brown planthopper (*Nilaparvata lugens*).

After the desired period of time, the effect in % is determined. 100% means that all planthoppers have been killed; 0% means that none of the planthoppers have been killed.

In this test, for example, the following compounds of the Preparation Examples show good activity: see table

| Example | Active compound concentration in g/ha | Kill rate in % after 7 days |
| --- | --- | --- |
| Example 10 | 100 | 100 |
| Example 13 | 100 | 100 |

Example No. 4

*Phaedon* Test (PHAECO Spray Treatment)

| | |
| --- | --- |
| Solvent: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Disks of Chinese cabbage (*Brassica pekinensis*) are sprayed with a preparation of active compound of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

In this test, for example, the following compounds of the Preparation Examples show good activity: see table

| Example | Active compound concentration in g/ha | Kill rate in % after 7 days |
| --- | --- | --- |
| Example 11 | 500 | 100 |
| Example 13 | 500 | 100 |
| Example 15 | 500 | 100 |
| Example 17 | 500 | 100 |

Example No. 5

*Meloidogyne* Test (MELGIN Spray Treatment)

| Solvent: | 80 parts by weight of acetone |
|---|---|

To produce a suitable preparation of active compound, 1 part by weight of active compound is mixed with the stated amounts of solvent, and the concentrate is diluted with water to the desired concentration.

Containers are filled with sand, active compound solution, *Meloidogyne incognita* egg/larvae suspension and lettuce seeds. The lettuce seeds germinate and the plants develop. On the roots, galls are formed.

After the desired period of time, the nematicidal activity is determined by the formation of galls in %. 100% means that no galls were found; 0% means that the number of galls on the treated plants corresponds to that of the untreated controls.

In this test, for example, the following compounds of the Preparation Examples show good activity: see table

| Example | Active compound concentration in ppm | Kill rate in % after 14 days |
|---|---|---|
| Example 10 | 20 | 80 |
| Example 11 | 20 | 100 |

Example No. 6

*Myzus persicae* Test, Hydroponic Treatment (MYZUPE sys.)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

The preparation of active compound is mixed with water. The stated concentration refers to the amount of active compound per volume unit of water (mg/l=ppm). The treated water is filled into containers housing a pea plant (*Pisum sativum*) which is then infected with the green peach aphid (*Myzus persicae*).

After the desired period of time, the kill in % is determined. 100% means that all aphids have been killed; 0% means that none of the aphids have been killed.

In this test, for example, the following compounds of the Preparation Examples show good activity: see table

| Example | Active compound concentration in ppm | Kill rate in % after 6 days |
|---|---|---|
| Example 10 | 20 | 100 |
| Example 11 | 20 | 100 |
| Example 14 | 20 | 100 |
| Example 13 | 20 | 100 |
| Example 15 | 4 | 100 |
| Example 8 | 4 | 98 |

Example No. 7

*Aphis gossypii* Test (APHIGO)

| Solvent: | 7 parts by weight of dimethylformamide |
|---|---|
| Emulsifier: | 2 parts by weight of alkylaryl polyglycol ether |

To produce a suitable preparation of active compound, 1 part with weight of active compound is mixed with the stated amounts of solvent and emulsifier, and the concentrate is diluted with emulsifier-containing water to the desired concentration.

Cotton leaves (*Gossypium hirsutum*) which are heavily infested with the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show good activity: see table

| Example | Active compound concentration in ppm | Kill rate in % after 6 days |
|---|---|---|
| Example 10 | 100 | 98 |
| Example 11 | 100 | 100 |
| Example 14 | 100 | 100 |
| Example 13 | 100 | 100 |
| Example 15 | 100 | 100 |
| Example 8 | 20 | 100 |

Example No. 8

*Aphis gossypii* Test; (APHIGO G)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

Cotton plants (*Gossypium hirsutum*) which are heavily infested with the cotton aphid (*Aphis gossypii*) are watered with a preparation of active compound of the desired concentration.

After the desired period of time, the kill in % is determined. 100% means that all aphids have been killed; 0% means that none of the aphids have been killed.

In this test, for example, the following compounds of the Preparation Examples show good activity: see table

| Example | Active compound concentration in ppm | Kill rate in % after 10 days |
|---|---|---|
| Example 10 | 4 | 100 |

Example No. 9

*Myzus persicae* Test; (MYZUPE G)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

Cabbage plants (*Brassica oleracea*) which are heavily infested with the green peach aphid (*Myzus persicae*) are watered with a preparation of active compound of the desired concentration.

After the desired period of time, the kill in % is determined. 100% means that all aphids have been killed; 0% means that none of the aphids have been killed.

In this test, for example, the following compounds of the Preparation Examples show good activity: see table

| Example | Active compound concentration in ppm | Kill rate in % after 10 days |
|---|---|---|
| Example 10 | 4 | 95 |

Example No. 10

*Bemisia tabaci* (BEMITA Spray Treatment)

| Solvent: | 78 parts by weight of acetone<br>1.5 parts by weight of dimethylformamide |
|---|---|
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Disks of cotton leaves (*Gossypium hirsutum*) which are infested with larvae of the whitefly (*Bemisia tabaci*) are sprayed with a preparation of active compound of the desired concentration.

After the desired period of time, the effect in % is determined. 100% means that all whiteflies have been killed; 0% means that none of the whiteflies have been killed.

In this test, for example, the following compounds of the Preparation Examples show good activity: see table

| Example | Active compound concentration in ppm | Kill rate in % after 7 days |
|---|---|---|
| Example 13 | 500 | 94 |

Example No. 11

*Ctenocephalides felis*; Oral (CTECFE)

| Solvent: dimethyl sulphoxide |
|---|

To produce a suitable preparation of active compound, 1 part by weight of active compound is mixed with the stated amount of solvent. Part of the concentrate is diluted with citrated cattle blood, and the desired concentration is prepared.

20 unfed adult fleas (*Ctenocephalides felis*) are placed into a chamber whose top and bottom ends are closed with gauze. A metal cylinder whose bottom end is closed with parafilm is placed onto the chamber. The cylinder contains the blood/active compound preparation, which can be taken up by the fleas through the parafilm membrane. The blood is warmed to 37° C., but the flea chamber is at room temperature.

After the desired period of time, the kill in % is determined. 100% means that all fleas have been killed; 0% means that none of the fleas have been killed.

In this test, for example, the following compounds of the Preparation Examples show good activity: see table

| Example | Active compound concentration in ppm | Kill rate in % after 2 days |
|---|---|---|
| Example 13 | 100 | 80 |
| Example 15 | 100 | 90 |

Example No. 12

*Lucilia* cuprina Test (LUCICU)

| Solvent: dimethyl sulphoxide |
|---|

To produce a suitable preparation of active compound, 1 part by weight of active compound is mixed with the stated amount of solvent, and the concentrate is diluted with water to the desired concentration.

Containers containing horse meat treated with the preparation of active compound of the desired concentration are populated with *Lucilia cuprina* larvae.

After the desired period of time, the kill in % is determined. 100% means that all larvae have been killed; 0% means that none of the larvae have been killed.

In this test, for example, the following compounds of the Preparation Examples show good activity: see table

| Example | Active compound concentration in ppm | Kill rate in % after 2 days |
|---|---|---|
| Example 11 | 100 | 100 |
| Example 13 | 100 | 100 |
| Example 15 | 100 | 90 |
| Example 8 | 100 | 100 |

Example No. 13

*Boophilus microplus* Test (BOOPMI Injection)

| Solvent: dimethyl sulphoxide |
|---|

To produce a suitable preparation of active compound, 1 part by weight of active compound is mixed with the stated amount of solvent, and the concentrate is diluted with solvent to the desired concentration.

The solution of active compound is injected into the abdomen (*Boophilus microplus*), and the animals are transferred into dishes and kept in a temperature-controlled room.

After the desired period of time, the effect in % is determined. 100% means that no tick has laid any fertile eggs.

In this test, for example, the following compounds of the Preparation Examples show good activity: see table

| Example | Active compound concentration in µg/animal | Kill rate in % after 7 days |
|---|---|---|
| Example 11 | 20 | 100 |

COMPARATIVE BIOLOGICAL EXAMPLES

Example No. 1

*Myzus persicae* Test (MYZUPE T)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested with the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show an activity superior to the prior art: see table

| Example | Active compound concentration in ppm | Kill rate in % after 6 days |
|---|---|---|
| Example 85 [a] | 20 | 15 |
| Example 86 [a] | 20 | 50 |
| Example 4 | 20 | 80 |
| Example 85 [a] | 20 | 15 |
| Example 1 | 20 | 95 |

[a] cf. EP 0539588 A1

Example No. 2

*Myzus* Test (MYZUPE Spray Treatment)

| Solvent: | 78 parts by weight of acetone |
|---|---|
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Disks of Chinese cabbage (*Brassica pekinensis*) which are infested with all stages of the green peach aphid (*Myzus persicae*) are sprayed with a preparation of active compound of the desired concentration.

After the desired period of time, the effect in % is determined. 100% means that all aphids have been killed; 0% means that none of the aphids have been killed.

In this test, for example, the following compounds of the Preparation Examples show an activity superior to the prior art: see table

| Example | Active compound concentration in g/ha | Kill rate in % after 5 days |
|---|---|---|
| Example 87 [a] | 100 | 0 |
| Example 9 | 100 | 90 |
| Example 176 [a] | 4 | 0 |
| Example 16 | 4 | 70 |
| Example 89 [a] | 4 | 0 |
| Example 1 | 4 | 80 |

[a] cf. EP 0539588 A1

Example No. 3

*Myzus persicae* Test, Hydroponic Treatment (MYZUPE sys.)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

The preparation of active compound is mixed with water. The stated concentration refers to the amount of active compound per volume unit of water (mg/l=ppm). The treated water is filled into containers housing a pea plant (*Pisum sativum*) which is then infected with the green peach aphid (*Myzus persicae*).

After the desired period of time, the kill in % is determined. 100% means that all aphids have been killed; 0% means that none of the aphids have been killed.

In this test, for example, the following compounds of the Preparation Examples show an activity superior to the prior art: see table

| Example | Active compound concentration in ppm | Kill rate in % after 6 days |
|---|---|---|
| Example 86 [a] | 0.8 | 75 |
|  | 0.16 | 0 |
| Example 4 | 0.8 | 100 |
|  | 0.16 | 55 |
| Example 85 [a] | 0.8 | 40 |
| Example 1 | 0.8 | 100 |

[a] cf. EP 0539588 A1

Example No. 4

*Myzus persicae* Test (MYZUPE)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration. If addition of ammonium salts or ammonium salts and penetrant is required, the appropriate amount is in each case pipetted in after dilution of the respective finished solution of the preparation.

Bell pepper plants (*Capsicum annuum*) which are heavily infested with the green peach aphid (*Myzus persicaei*) are treated by spraying with the preparation of active compound in the desired concentration.

After the desired period of time, the kill in % is determined. 100% means that all animals have been killed; 0% means that none of the animals have been killed.

Example No. 5

*Myzus* Test Oral (MYZUPE O)

| Solvent: | 80 parts by weight of acetone |
|---|---|

To produce a suitable preparation of active compound, 1 part by weight of active compound is mixed with the stated amounts of solvent, and the concentrate is diluted with water to the desired concentration.

Containers are populated with all stages of the green peach aphid (*Myzus persicae*), treatment is by sucking at the preparation of active compound of the desired concentration.

After the desired period of time, the effect in % is determined. 100% means that all aphids have been killed; 0% means that none of the aphids have been killed.

In this test, for example, the following compounds of the Preparation Examples show an activity superior to the prior art: see table

| Example | Active compound concentration in ppm | Kill rate in % after 5 days |
|---|---|---|
| Example 85 [a] | 0.032 | 0 |
| Example 1 | 0.032 | 100 |

[a] cf. EP 0539588 A1

Example No. 6

*Aphis gossypii* Test (APHIGO)

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested with the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show good activity: see table

| Example | Active compound concentration in ppm | Kill rate in % after 6 days |
|---|---|---|
| Example 85 [a] | 4 | 45 |
| Example 86 [a] | 4 | 10 |
| Example 4 | 4 | 99 |

-continued

| Example | Active compound concentration in ppm | Kill rate in % after 6 days |
|---|---|---|
| Example 85 [a] | 4 | 45 |
|  | 0.8 | 15 |
| Example 1 | 4 | 98 |
|  | 0.8 | 60 |

[a] cf. EP 0539588 A1

Example No. 7

*Meloidogyne* Test (MELGIN Spray Treatment)

| Solvent: | 80 parts by weight of acetone |
|---|---|

To produce a suitable preparation of active compound, 1 part by weight of active compound is mixed with the stated amount of solvent, and the concentrate is diluted with water to the desired concentration.

Containers are filled with sand, active compound solution, *Meloidogyne incognita* egg/larvae suspension and lettuce seeds. The lettuce seeds germinate and the plants develop. On the roots, galls are formed.

After the desired period of time, the nematicidal activity is determined by the formation of galls in %. 100% means that no galls were found; 0% means that the number of galls on the treated plants corresponds to that of the untreated controls.

In this test, for example, the following compounds of the Preparation Examples show an activity superior to the prior art: see table

| Example | Active compound concentration in ppm | Kill rate in % after 14 days |
|---|---|---|
| Example 85 [a] | 20 | 0 |
| Example 4 | 20 | 70 |

[a] cf. EP 0539588 A1

Example No. 8

*Lucilia cuprina* Test (LUCICU)

| Solvent: dimethyl sulphoxide |
|---|

To produce a suitable preparation of active compound, 1 part by weight of active compound is mixed with the stated amount of solvent, and the concentrate is diluted with water to the desired concentration.

Containers containing horse meat treated with the preparation of active compound of the desired concentration are populated with *Lucilia cuprina* larvae.

After the desired period of time, the kill in % is determined. 100% means that all larvae have been killed; 0% means that none of the larvae have been killed.

In this test, for example, the following compounds of the Preparation Examples show an activity superior to the prior art: see table

| Example | Active compound concentration in ppm | Kill rate in % after 2 days |
|---|---|---|
| Example 85 [a] | 4 | 45 |
| Example 1 | 4 | 100 |

[a] cf. EP 0539588 A1

Example No. 9

*Ctenocephalides felis*; Oral (CTECFE)

| Solvent: dimethyl sulphoxide |
|---|

To produce a suitable preparation of active compound, 1 part by weight of active compound is mixed with the stated amount of solvent. Part of the concentrate is diluted with citrated cattle blood, and the desired concentration is prepared.

20 unfed adult fleas (*Ctenocephalides felis*) are placed into a chamber whose top and bottom ends are closed with gauze. A metal cylinder whose bottom end is closed with parafilm is placed onto the chamber. The cylinder contains the blood/active compound preparation, which can be taken up by the fleas through the parafilm membrane. The blood is warmed to 37° C., but the flea chamber is at room temperature.

After the desired period of time, the kill in % is determined. 100% means that all fleas have been killed; 0% means that none of the fleas have been killed.

In this test, for example, the following compounds of the Preparation Examples show an activity superior to the prior art: see table

| Example | Active compound concentration in ppm | Kill rate in % after 1 day |
|---|---|---|
| Example 85 [a] | 100 | 0 |
| Example 86 [a] | 100 | 0 |
| Example 4 | 100 | 30 |

[a] cf. EP 0539588 A1

Example No. 10

*Boophilus microplus* Test (BOOPMI Injection)

| Solvent: dimethyl sulphoxide |
|---|

To produce a suitable preparation of active compound, 1 part by weight of active compound is mixed with the stated amount of solvent, and the concentrate is diluted with solvent to the desired concentration.

The solution of active compound is injected into the abdomen (*Boophilus microplus*), and the animals are transferred into dishes and kept in a temperature-controlled room.

After the desired period of time, the effect in % is determined. 100% means that no tick has laid any fertile eggs.

In this test, for example, the following compounds of the Preparation Examples show an activity superior to the prior art: see table

| Example | Active compound concentration in ppm | Kill rate in % after 7 days |
|---|---|---|
| Example 85 [a] | 20 | 0 |
| Example 86 [a] | 20 | 0 |
| Example 4 | 20 | 100 |

[a] cf. EP 0539588 A1

The invention claimed is:

1. A method for the manufacture of a compound of the formula (I)

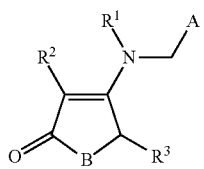
(I)

in which
A represents pyrid-3-yl which is optionally substituted in the 6-position by fluorine, chlorine, bromine or trifluoromethyl, or represents 1,3-thiazol-5-yl which is optionally substituted in the 2-position by chlorine;
B represents oxygen, sulphur or methylene;
$R^1$ represents halo-$C_1$-$C_3$-alkyl or halo-$C_2$-$C_3$-alkenyl;
$R^2$ represents hydrogen or halogen; and
$R^3$ represents hydrogen or methyl;
which method comprises reacting a compound of the formula (II)

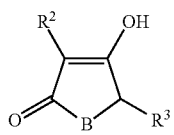
(II)

in which
B represents oxygen, sulphur or methylene;
$R^2$ represents hydrogen or halogen; and
$R^3$ represents hydrogen or methyl;
with a compound of the formula (III)

$$HN(R^1)-CH_2-A \qquad (III)$$

in which
A represents pyrid-3-yl which is optionally substituted in the 6-position by fluorine, chlorine, bromine or trifluoromethyl, or represents 1,3-thiazol-5-yl which is optionally substituted in the 2-position by chlorine; and
$R^1$ represents halo-$C_1$-$C_3$-alkyl or halo-$C_2$-$C_3$-alkenyl;
in the presence of an acidic auxiliary selected from p-toluenesulfonic acid or acetic acid, optionally in the presence of a suitable diluent.

2. The method according to claim 1 in which
A represents 6-fluoropyrid-3-yl, 6-chloropyrid-3-yl, 6-bromopyrid-3-yl, 6-trifluoromethylpyrid-3-yl, or 2-chloro-1,3-thiazol-5-yl;
B represents oxygen or methylene;
$R^1$ represents fluorine-substituted $C_1$-$C_3$-alkyl or $C_2$-$C_3$-alkenyl;
$R^2$ represents hydrogen or halogen; and
$R^3$ represents hydrogen or methyl.

3. The method according to claim 1, wherein the suitable diluent is present and is selected from benzene, toluene, chlorobenzene, bromobenzene, nitrobenzene or xylene.

4. The method according to claim 2, wherein the suitable diluent is present and is selected from benzene, toluene, chlorobenzene, bromobenzene, nitrobenzene or xylene.

5. A method according to claim 1, wherein the reaction is carried out at temperatures between 60° C. and 140° C.

6. A method according to claim 1, wherein the compound of the formula (II) is tetronic acid and the compound of the formula (III) is N-[(6-chloropyridin-3-yl)methyl]-2,2-difluoroethane-1-amine.

* * * * *